(12) United States Patent
Vlieghe et al.

(10) Patent No.: US 8,877,716 B2
(45) Date of Patent: *Nov. 4, 2014

(54) PEPTIDE DERIVATIVES, PREPARATION AND USES THEREOF

(71) Applicant: Vect-Horus, Marseilles Cedex 15 (FR)

(72) Inventors: Patrick Vlieghe, Bandol (FR); Marion David, Marseilles (FR); Yves Molino, Carry le Rouet (FR); Michel Khrestchatisky, Marseilles (FR)

(73) Assignees: Vect-Horus, Marseille Cedex (FR); Centre National de la Recherche Scientifique, Paris (FR); Universite D'Aix-Marseille, Marseille Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/655,954

(22) Filed: Oct. 19, 2012

(65) Prior Publication Data

US 2013/0108548 A1 May 2, 2013

Related U.S. Application Data

(63) Continuation-in-part of application No. PCT/FR2011/050883, filed on Apr. 18, 2011.

(30) Foreign Application Priority Data

Apr. 21, 2010 (FR) ..................... 10 53036

(51) Int. Cl.
| | |
|---|---|
| A61K 38/16 | (2006.01) |
| C07K 4/00 | (2006.01) |
| C07K 7/50 | (2006.01) |
| C07K 7/06 | (2006.01) |
| C07K 7/02 | (2006.01) |
| C07K 7/64 | (2006.01) |
| C07K 14/775 | (2006.01) |
| A61K 47/48 | (2006.01) |

(52) U.S. Cl.
CPC .............. *C07K 7/06* (2013.01); *C07K 2319/33* (2013.01); *C07K 2319/74* (2013.01); *C07K 7/02* (2013.01); *C07K 7/64* (2013.01); *C07K 14/775* (2013.01); *C07K 7/50* (2013.01); *A61K 47/48246* (2013.01); *A61K 47/48238* (2013.01)
USPC ........................ 514/21.3; 530/300; 530/317

(58) Field of Classification Search
CPC .................. A61K 47/48246; A61K 47/48238; C07K 7/06; C07K 14/775; C07K 2319/33; C07K 2319/74; C07K 7/02; C07K 7/50; C07K 7/64

See application file for complete search history.

(56) References Cited

U.S. PATENT DOCUMENTS

2004/0031072 A1* 2/2004 La Rosa et al. ............... 800/278

FOREIGN PATENT DOCUMENTS

| CA | 2 796 174 | 10/2011 |
| WO | WO 99/47566 | 9/1999 |
| WO | WO 2011/131896 | 10/2011 |

OTHER PUBLICATIONS

Definitation of analog and analogue, from http://cancerweb.ncl.ac.uk/cgi-bin/omd?query=analog, pp. 1-5, accessed Jul. 7, 2005.*
Voet, D. et al. Biochemistry Second Edition, *John Wiley & Sons, Inc.*, 1995, pp. 235-241.
Definitions of analog and analogue, from http://cancerweb.ncl.ac.uk/cgi-bin/omd?query=analog, pp. 1-5, accessed Jul. 7, 2005.
Ngo, J. Thomas, et al. "Computational Complexity, Protein Structure Prediction, and the Levinthal Paradox" *The Protein Folding Problem and Tertiary Structure Prediction*,1994, pp. 491-494.
Rudinger, J. "Characteristics of the amino acids as components of a peptide hormone sequence" *Peptide Hormones*, Jun. 1976, 1-7.
Bradley, Christina, et al. "Limits of Cooperativity in a Structurally Modular Protein: Response of the Notch Ankyrin Domain to Analogous Alanine Substitutions in Each Repeat" *J. Mol. Biol.*, 2002, pp. 373-386, vol. 324.
Berendsen, Herman J.C. "A Glimpse of the Holy Grail?" *Science*, Oct. 23, 1998, pp. 642-643, vol. 282.
SIGMA, "Designing Custom Peptides" 2004, pp. 1-2.

* cited by examiner

*Primary Examiner* — Julie Ha
*Assistant Examiner* — Li Ni Komatsu
(74) *Attorney, Agent, or Firm* — Saliwanchik Lloyd & Eisenschenk

(57) ABSTRACT

The invention relates to peptide derivatives (peptides and pseudo-peptides) and the use thereof as vectors for molecules of interest. The invention also relates to conjugates containing a peptide derivative of the invention bound to a molecule of interest. The peptides of the invention can be used, in particular, to vectorize, generally in the form of prodrug conjugates, molecules of pharmaceutical or diagnostic interest such as, for example, therapeutic molecules, imaging or diagnostic agents, or molecular probes, across cell membranes of different tissues or organs, healthy or pathologic, and in particular to enable their transport across physiological barriers of the nervous system such as the Blood brain barrier (BBB), Blood-spinal cord barrier (BSCB), or Blood-retinal barrier (BRB).

18 Claims, 14 Drawing Sheets
(5 of 14 Drawing Sheet(s) Filed in Color)

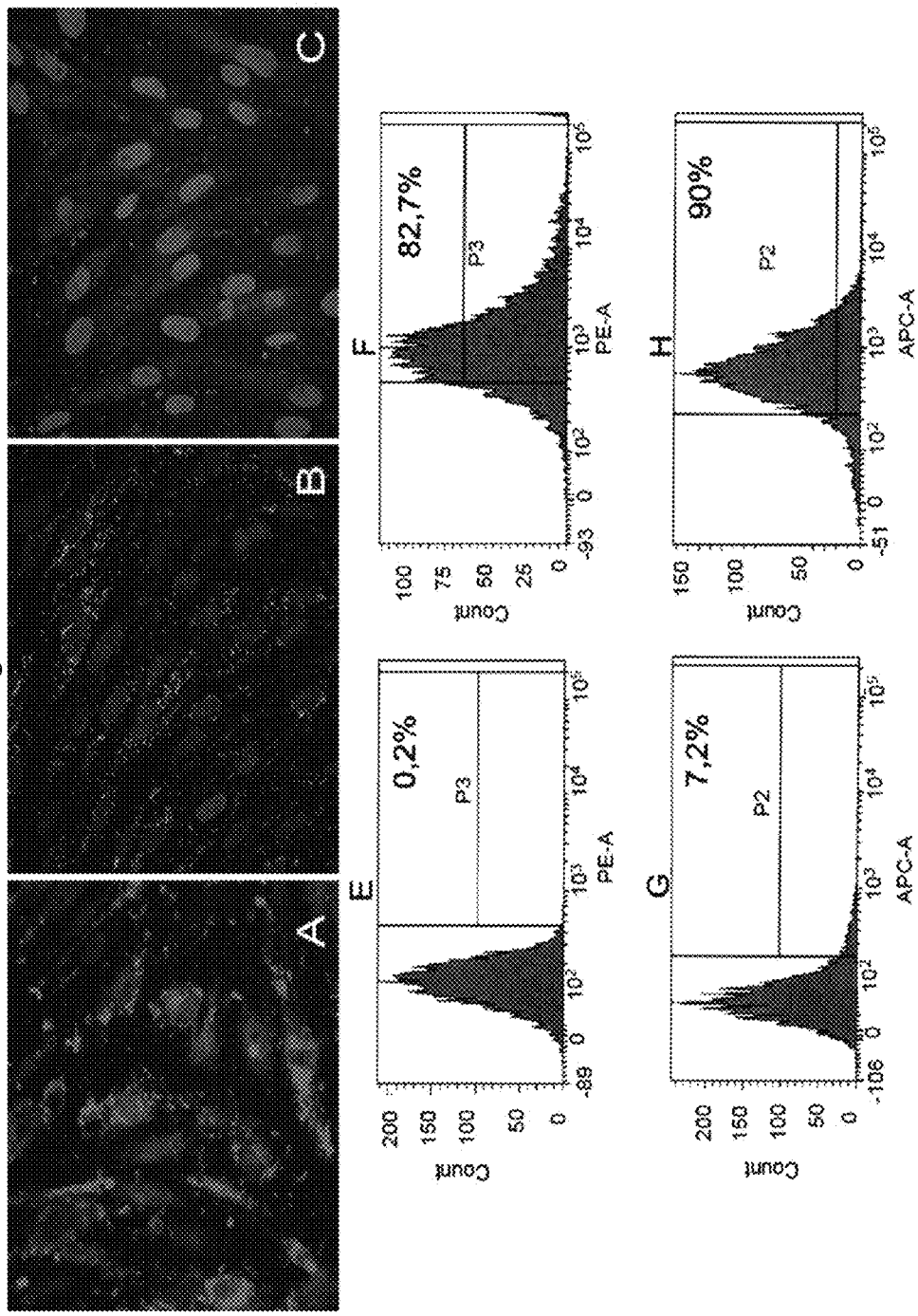

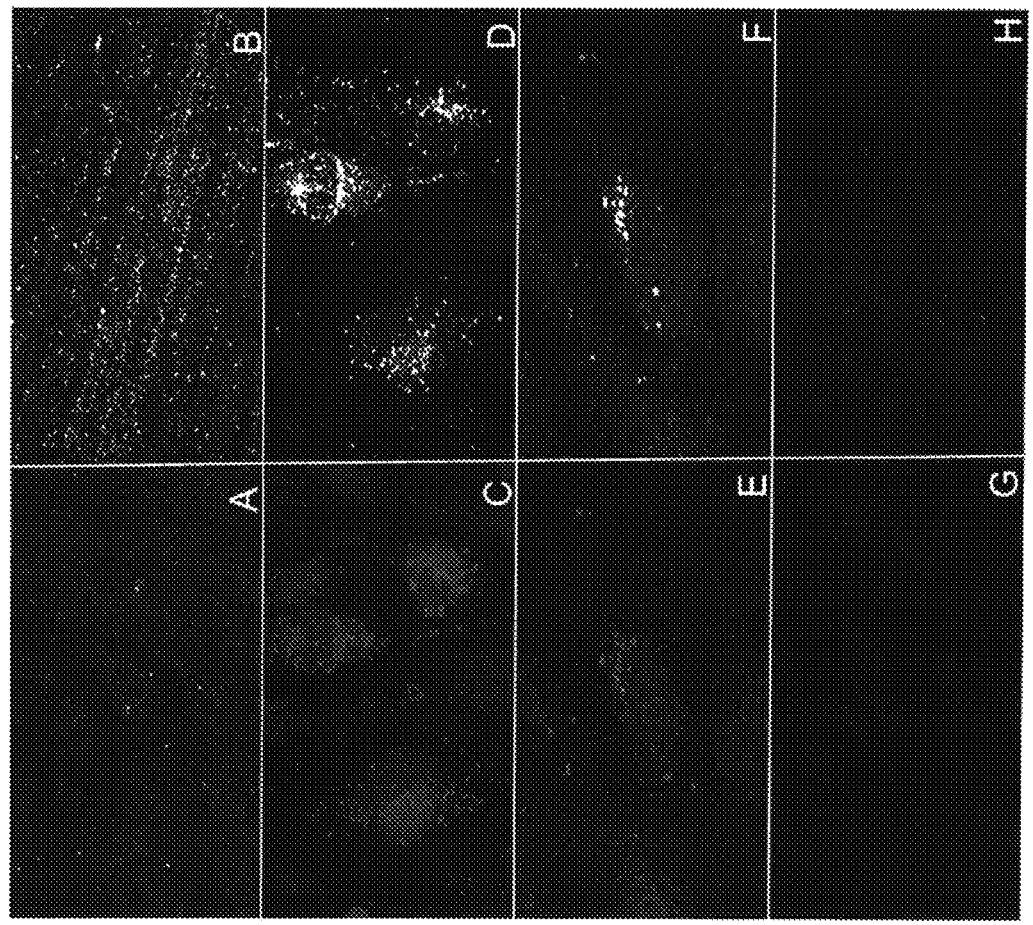

SEQUENCE LISTING

```
<160> NUMBER OF SEQ ID NOS: 31

<210> SEQ ID NO 1
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys
<220> FEATURE:
<221> NAME/KEY: MISC_FEATURE
<222> LOCATION: (3)..(3)
<223> OTHER INFORMATION: Xaa = Pip

<400> SEQUENCE: 1

Xaa Met Xaa Arg Leu Arg Gly Cys
1               5

<210> SEQ ID NO 2
<211> LENGTH: 8
<212> TYPE: PRT
<213> ORGANISM: Artificial sequence
<220> FEATURE:
```

```
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-pen
<220> FEATURE:
<221> NAME/KEY: MISC_FEATURE
<222> LOCATION: (3)..(3)
<223> OTHER INFORMATION: Xaa = Pip

<400> SEQUENCE: 2

Xaa Met Xaa Arg Leu Arg Gly Cys
1               5

<210> SEQ ID NO 3
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = Pen
<220> FEATURE:
<221> NAME/KEY: MISC_FEATURE
<222> LOCATION: (3)..(3)
<223> OTHER INFORMATION: Xaa = Pip

<400> SEQUENCE: 3

Xaa Met Xaa Arg Leu Arg Gly Cys
1               5

<210> SEQ ID NO 4
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys
<220> FEATURE:
<221> NAME/KEY: MISC_FEATURE
<222> LOCATION: (3)..(3)
<223> OTHER INFORMATION: Xaa = Thz

<400> SEQUENCE: 4

Xaa Met Xaa Arg Leu Arg Gly Cys
1               5

<210> SEQ ID NO 5
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-pen
<220> FEATURE:
<221> NAME/KEY: MISC_FEATURE
<222> LOCATION: (3)..(3)
<223> OTHER INFORMATION: Xaa = Thz

<400> SEQUENCE: 5

Xaa Met Xaa Arg Leu Arg Gly Cys
1               5
```

```
<210> SEQ ID NO 6
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = Pen
<220> FEATURE:
<221> NAME/KEY: MISC_FEATURE
<222> LOCATION: (3)..(3)
<223> OTHER INFORMATION: Xaa = Thz

<400> SEQUENCE: 6

Xaa Met Xaa Arg Leu Arg Gly Cys
1               5

<210> SEQ ID NO 7
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys
<220> FEATURE:
<221> NAME/KEY: MISC_FEATURE
<222> LOCATION: (3)..(3)
<223> OTHER INFORMATION: Xaa = Thz
<220> FEATURE:
<221> NAME/KEY: MISC_FEATURE
<222> LOCATION: (7)..(7)
<223> OTHER INFORMATION: Xaa = Sar

<400> SEQUENCE: 7

Xaa Met Xaa Arg Leu Arg Xaa Cys
1               5

<210> SEQ ID NO 8
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-pen
<220> FEATURE:
<221> NAME/KEY: MISC_FEATURE
<222> LOCATION: (3)..(3)
<223> OTHER INFORMATION: Xaa = Thz
<220> FEATURE:
<221> NAME/KEY: MISC_FEATURE
<222> LOCATION: (7)..(7)
<223> OTHER INFORMATION: Xaa = Sar

<400> SEQUENCE: 8

Xaa Met Xaa Arg Leu Arg Xaa Cys
1               5

<210> SEQ ID NO 9
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
```

```
<222> LOCATION: (1)..(1)
<223> OTHER INFORMATION: Xaa = Pen
<220> FEATURE:
<221> NAME/KEY: MISC_FEATURE
<222> LOCATION: (3)..(3)
<223> OTHER INFORMATION: Xaa = Thz
<220> FEATURE:
<221> NAME/KEY: MISC_FEATURE
<222> LOCATION: (7)..(7)
<223> OTHER INFORMATION: Xaa = Sar

<400> SEQUENCE: 9

Xaa Met Xaa Arg Leu Arg Xaa Cys
1               5

<210> SEQ ID NO 10
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Cys at position 1 is in configuration D
<220> FEATURE:
<221> NAME/KEY: MISC_FEATURE
<222> LOCATION: (7)..(7)
<223> OTHER INFORMATION: Ala at position 7 is in configuration D

<400> SEQUENCE: 10

Cys Met Pro Arg Leu Arg Ala Cys
1               5

<210> SEQ ID NO 11
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys
<220> FEATURE:
<221> NAME/KEY: MISC_FEATURE
<222> LOCATION: (4)..(4)
<223> OTHER INFORMATION: Xaa = hArg

<400> SEQUENCE: 11

Xaa Met Pro Xaa Leu Arg Gly Cys
1               5

<210> SEQ ID NO 12
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys
<220> FEATURE:
<221> NAME/KEY: MISC_FEATURE
<222> LOCATION: (4)..(4)
<223> OTHER INFORMATION: Xaa = Agb

<400> SEQUENCE: 12

Xaa Met Pro Xaa Leu Arg Gly Cys
1               5
```

```
<210> SEQ ID NO 13
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys
<220> FEATURE:
<221> NAME/KEY: MISC_FEATURE
<222> LOCATION: (4)..(4)
<223> OTHER INFORMATION: Xaa = Agp

<400> SEQUENCE: 13

Xaa Met Pro Xaa Leu Arg Gly Cys
1               5

<210> SEQ ID NO 14
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys
<220> FEATURE:
<221> NAME/KEY: MISC_FEATURE
<222> LOCATION: (4)..(4)
<223> OTHER INFORMATION: Xaa = Cit

<400> SEQUENCE: 14

Xaa Met Pro Xaa Leu Arg Gly Cys
1               5

<210> SEQ ID NO 15
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys
<220> FEATURE:
<221> NAME/KEY: MISC_FEATURE
<222> LOCATION: (6)..(6)
<223> OTHER INFORMATION: Xaa = Cit

<400> SEQUENCE: 15

Xaa Met Pro Arg Leu Xaa Gly Cys
1               5

<210> SEQ ID NO 16
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys
<220> FEATURE:
<221> NAME/KEY: MISC_FEATURE
<222> LOCATION: (6)..(6)
<223> OTHER INFORMATION: Xaa = Arg(NO2)
```

```
<400> SEQUENCE: 16

Xaa Met Pro Arg Leu Xaa Gly Cys
1               5

<210> SEQ ID NO 17
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa = (D)-cys

<400> SEQUENCE: 17

Xaa Met Pro Arg Leu Arg Gly Cys
1               5

<210> SEQ ID NO 18
<211> LENGTH: 34
<212> TYPE: DNA
<213> ORGANISM: Artificial sequence
<220> FEATURE:
<223> OTHER INFORMATION: hLDLR forward primer

<400> SEQUENCE: 18
atatataagc ttcgaggaca cagcaggtcg tgat                              34

<210> SEQ ID NO 19
<211> LENGTH: 35
<212> TYPE: DNA
<213> ORGANISM: Artificial sequence
<220> FEATURE:
<223> OTHER INFORMATION: hLDLR reverse primer

<400> SEQUENCE: 19
ttaattgtcg accacgccac gtcatcctcc agact                             35

<210> SEQ ID NO 20
<211> LENGTH: 32
<212> TYPE: DNA
<213> ORGANISM: Artificial sequence
<220> FEATURE:
<223> OTHER INFORMATION: mLDLR forward primer

<400> SEQUENCE: 20
atatataagc ttgacgcaac gcagaagcta ag                                32

<210> SEQ ID NO 21
<211> LENGTH: 32
<212> TYPE: DNA
<213> ORGANISM: Artificial sequence
<220> FEATURE:
<223> OTHER INFORMATION: mLDLR reverse primer

<400> SEQUENCE: 21
ttaattggta ccgttgccac atcgtcctcc ag                                32

<210> SEQ ID NO 22
<211> LENGTH: 32
<212> TYPE: DNA
<213> ORGANISM: Artificial sequence
<220> FEATURE:
<223> OTHER INFORMATION: rLDLR forward primer

<400> SEQUENCE: 22
```

```
atatataagc ttacatttcg ggtctgtgat cc                                    32
```

<210> SEQ ID NO 23
<211> LENGTH: 32
<212> TYPE: DNA
<213> ORGANISM: Artificial sequence
<220> FEATURE:
<223> OTHER INFORMATION: rLDLR reverse primer

<400> SEQUENCE: 23

```
ttaattggta cccatgccac atcatcctcc ag                                    32
```

<210> SEQ ID NO 24
<211> LENGTH: 20
<212> TYPE: DNA
<213> ORGANISM: Artificial sequence
<220> FEATURE:
<223> OTHER INFORMATION: Forward primer

<400> SEQUENCE: 24

```
cttggcatta tgcacctcca                                                  20
```

<210> SEQ ID NO 25
<211> LENGTH: 67
<212> TYPE: DNA
<213> ORGANISM: Artificial sequence
<220> FEATURE:
<223> OTHER INFORMATION: Reverse primer

<400> SEQUENCE: 25

```
ctggccagct agcactcagc aaccgcgaag acgaggcata caagcacctt tacccggaga      60
cagggag                                                                67
```

<210> SEQ ID NO 26
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (3)..(3)
<223> OTHER INFORMATION: Xaa = Thz
<220> FEATURE:
<221> NAME/KEY: MISC_FEATURE
<222> LOCATION: (8)..(8)
<223> OTHER INFORMATION: Xaa = Pen

<400> SEQUENCE: 26

```
Cys Met Xaa Arg Leu Arg Gly Xaa
1               5
```

<210> SEQ ID NO 27
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (3)..(3)
<223> OTHER INFORMATION: Xaa = Thz
<220> FEATURE:
<221> NAME/KEY: MISC_FEATURE
<222> LOCATION: (7)..(7)
<223> OTHER INFORMATION: Xaa = Sar
<220> FEATURE:
<221> NAME/KEY: MISC_FEATURE

```
<222> LOCATION: (8)..(8)
<223> OTHER INFORMATION: Xaa = Pen

<400> SEQUENCE: 27

Cys Met Xaa Arg Leu Arg Xaa Xaa
1               5

<210> SEQ ID NO 28
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (3)..(3)
<223> OTHER INFORMATION: Xaa = Pip
<220> FEATURE:
<221> NAME/KEY: MISC_FEATURE
<222> LOCATION: (7)..(7)
<223> OTHER INFORMATION: Xaa = Sar

<400> SEQUENCE: 28

Cys Met Xaa Arg Leu Arg Xaa Cys
1               5

<210> SEQ ID NO 29
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (3)..(3)
<223> OTHER INFORMATION: Xaa = Pip
<220> FEATURE:
<221> NAME/KEY: MISC_FEATURE
<222> LOCATION: (8)..(8)
<223> OTHER INFORMATION: Xaa = Pen

<400> SEQUENCE: 29

Cys Met Xaa Arg Leu Arg Gly Xaa
1               5

<210> SEQ ID NO 30
<211> LENGTH: 8
<212> TYPE: PRT
<213> ORGANISM: Artificial sequence
<220> FEATURE:
<223> OTHER INFORMATION: synthesized
<220> FEATURE:
<221> NAME/KEY: MISC_FEATURE
<222> LOCATION: (3)..(3)
<223> OTHER INFORMATION: Xaa = Pip
<220> FEATURE:
<221> NAME/KEY: MISC_FEATURE
<222> LOCATION: (7)..(7)
<223> OTHER INFORMATION: Xaa = Sar
<220> FEATURE:
<221> NAME/KEY: MISC_FEATURE
<222> LOCATION: (8)..(8)
<223> OTHER INFORMATION: Xaa = Pen

<400> SEQUENCE: 30

Cys Met Xaa Arg Leu Arg Xaa Xaa
1               5

<210> SEQ ID NO 31
<211> LENGTH: 8
<212> TYPE: PRT
```

```
<213> ORGANISM: Artificial sequence
<220> FEATURE:
<223> OTHER INFORMATION: synthesized

<400> SEQUENCE: 31

Cys Met Pro Arg Leu Arg Gly Cys
1               5
```

PEPTIDE DERIVATIVES, PREPARATION AND USES THEREOF

CROSS-REFERENCE TO RELATED APPLICATION

This application is a continuation-in-part of International Application No. PCT/FR2011/050883, filed Apr. 18, 2011, the disclosure of which is hereby incorporated by reference in its entirety, including all figures, tables and amino acid or nucleic acid sequences.

The Sequence Listing for this application is labeled "SeqList-replace.txt" which was created on Dec. 28, 2012 and is 10 KB. The entire contents of the sequence listing is incorporated herein by reference in its entirety.

The invention relates to peptide derivatives (peptides and pseudo-peptides) and the use thereof as vectors for molecules of interest. The invention also relates to conjugates containing a peptide derivative of the invention bound to a molecule of interest. The peptides of the invention can be used, in particular, to vectorize, generally in the form of prodrug conjugates, molecules of pharmaceutical or diagnostic interest such as, for example, therapeutic molecules, imaging or diagnostic agents, or molecular probes, across cell membranes of different tissues or organs, healthy or pathologic, and in particular to enable their transport across physiological barriers of the nervous system such as the Blood brain barrier (BBB), Blood-spinal cord barrier (BSCB), or Blood-retinal barrier (BRB).

CONTEXT OF THE INVENTION

According to *IMS Health*, the global market for drugs for treating central nervous system (CNS, brain and spinal cord) pathologies was approximately 70 billion dollars in 2007, with nearly 9 billion dollars of this amount representing products arising from drug delivery technologies (Jain, 2008, *Jain PharmaBiotech Report, Drug Delivery in CNS disorders*). Thus, neurology is today one of the three largest therapeutic areas, along with cardiovascular medicine and oncology. Although the number of people suffering from CNS disorders and pathologies throughout the world is larger than that of people with cardiovascular diseases or cancers, neurology remains an under-developed market. This is explained in part by the fact that 98% of potential drugs for treating CNS pathologies do not cross the blood-brain barrier or BBB (Pardridge, 2003, *Mol. Interv.*, 3, 90-105). Only 5% of the drugs presently on the market relate to the nervous system.

Indeed, the central nervous system (CNS, brain, spinal cord) is protected from potentially toxic substances by the presence of two principal physiological barrier systems: the BBB/BSCB, and the blood-cerebrospinal fluid barrier (BC-SFB). The BBB is regarded as the principal route for the uptake of plasma ligands at the brain level. Its surface area is approximately 5000 times larger than that of the BCSFB. The overall length of the constitutive blood vessels of the BBB is approximately 600 km. Each cm³ of cerebral cortex contains the equivalent of 1 km of blood vessels. The total surface area of the BBB is estimated at 20 m² (De Boer et al., 2007, *Clin. Pharmacokinet.*, 46(7), 553-576). The BBB and BSCB are regarded as major obstacles to overcome in the development of novel therapies for treating CNS pathologies and injuries (Neuwelt et al., 2008, *Lancet Neurol.*, 7, 84-96).

Similarly, in the eye, the blood-retinal barrier (BRB), is part of the blood-ocular barrier that consists of cells that are also joined tightly together and that prevent certain substances from entering the retina. The BRB has two components: the retinal vascular endothelium and the retinal pigment epithelium also referred to as inner and outer components (inner BRB [iBRB] and outer BRB [oBRB]). Retinal blood vessels that are similar to cerebral blood vessels maintain the inner blood-ocular barrier. Like the BBB or BSCB this physiological barrier comprises a single layer of non-fenestrated endothelial cells, with tight junctions (TJ). These junctions between retinal epithelial cells prevent passage of large molecules from choriocapillaris into the retina.

In 2007, the total worldwide ophthalmic pharmaceutical sector was valued at approximately $11.52 billion (Visiongain, *Ophthalmics*. 2007, Visiongain, Inc.: San Francisco. Janoria K G, et al. *Novel approaches to retinal drug delivery. Expert Opin Drug Deliv.* 2007; 4 (4): 371-388). Retinal diseases include retinitis pigmentosa, macular degeneration, cone-rod dystrophy (CORD), retinal separation, retinal detachment, hypertensive retinopathy and diabetic retinopathy, retinoblastoma, lipemia retinalis etc.

Due to the increasing age of many populations, financial experts forecast average yearly expansion in the sector to be greater than 10% over the near term. Nonetheless, the sustained delivery of therapeutically effective concentrations of drug to treat diseases of the eye, particularly diseases of the posterior segment of the eye, remains a significant technological challenge. The corresponding problem of patient compliance with existing therapies is a critical issue as well. Thus, substantial market opportunities exist for companies that pursue novel molecules as well as innovative drug delivery systems.

Thus, BBB, BSCB, and BRB represent major obstacles to the use of potential drugs against many CNS and eye disorders, but also a large surface of potential exchange between the blood and nervous tissue.

As a general rule, only a few small lipophilic molecules of approximately 450 to 600 Daltons (only 2% of drug candidates) can pass through the above-mentioned physiological barriers, that is to say, pass from the blood to the nervous tissue. The molecular weight and the size of many drug candidates, which show promising results in in vitro studies and in animal studies for treating CNS disorders, are considerably larger. Thus, most molecules such as therapeutic peptides, proteins, including therapeutic antibodies are generally excluded from passage/transport from the blood to nervous tissue in the CNS or the eye (retina), because of the low transcellular permeability of nervous tissue capillary endothelial cells. Brain capillary endothelial cells (BCECs) organized in vessels are surrounded by a basal lamina, astrocyte end-feet, pericytes and microglial and neuronal cells. The tight association of endothelial cells with astrocyte end-feet is responsible for the development and maintenance of properties of BBB impermeability to most molecules, thus ensuring strict and effective control of molecular exchanges between the blood and the brain in order to maintain brain homeostasis. Endothelial cells are closely bound by TJ, compared with endothelial cells of other organs, which are fenestrated. These TJ thus prevent paracellular passage across the BBB. Endothelial cells and the astrocyte end-feet which surround them also constitute a physiological barrier, since these cells have effective efflux systems which restrict any passage/transport by the transcellular route. Indeed, certain molecules capable of crossing physiological barriers are actively expelled from the endothelial cells towards the blood system by multidrug resistant (MDR) transport proteins. These active efflux transport (AET) systems generally control the active efflux of small molecules from the nervous tissue towards the blood system. As an example, the model AET system at the BBB is the ATP binding cassette (ABC) transporter, namely P-glycoprotein (P-gp); however, other AET systems are present at the BBB such as MDR-associated protein 1 (MRP1). P-gp, which is principally located on the luminal surface of BCECs is an essential element in the function of the physiological barrier of the BBB preventing entry into the brain of most xenobiotics but also drug candidates and other molecules of therapeutic interest capable of being active in the CNS. These properties thus strongly limit the passage of substances from the blood plasma towards the extracellular space of nervous tissues in the CNS and the eye.

One of the reasons that may explain why no really effective treatment is currently available for the principal CNS or ocular pathologies and injuries (brain cancer, Parkinson's and Alzheimer's diseases, cerebrovascular accidents (CVA), etc.) is that developers of drug candidates for treating brain pathologies carry out in-house research programs (brain drug-discovery programs) while investing little effort in the problems of passing the barriers and in the preferential targeting of nervous tissues, and notably of the brain (brain drug-targeting programs), (Pardridge, 2003, *Mol. Interv.*, 3, 90-105). A drug candidate must follow certain structural, physicochemical, pharmacochemical and pharmacological rules in order to have the best chances of becoming a drug for treating a CNS pathology or disorder (Pajouhesh et al., 2005, *NeuroRx*, 2(4), 541-553). Thus, in the development of a drug candidate, the selectivity and specificity (pharmacological profiling) of a molecule for its target are essential to its therapeutic activity (effectiveness). The bioavailability and potential toxicity (pharmaceutical profiling) of a molecule are crucial for its future as a drug. In other words, any molecule likely to become a drug for treating a CNS or ocular pathology or disorder must move across the BBB/BSCB or the BRB, maintain its biological activity, and exhibit suitable properties of pharmacokinetics (PK), absorption, distribution, metabolism and excretion/elimination (ADME) and pharmacodynamics (PD), with low toxicity (Tox). In fact, the hydrophilic/lipophilic balance of the molecule under development is particularly difficult to find for medicinal chemists in this field of nervous system therapeutics.

One of the major problems in treating CNS disorders and pathologies thus lies in the fact that the molecules administered do not pass the BBB/BSCB/BRB and thus cannot reach their target(s) in the CNS or the eye. One of the priorities of research in the discovery of molecules for treating, diagnosing or imaging CNS or ocular disorders or pathologies is thus to find means for increasing the effectiveness of passage of active substances across the BBB/BSCB or BRB.

In this respect, strategies for the vectorization of molecules across these barriers, currently studied and used by developers of drug candidates in order to enable a molecule of therapeutic interest to reach the CNS, can be divided into two principal strategies: pharmacological approaches and physiological approaches (FIG. 1), (Pardridge, 2007, *Pharm. Res.*, 24(9), 1733-1744; De Boer et al., 2007, *Clin. Pharmacokinet.*, 46(7), 553-576; De Boer et al., 2007, *Annu. Rev. Pharmacol. Toxicol.*, 47, 327-355; Jones et al., 2007, *Pharm. Res.*, 24(9), 1759-1771).

Invasive Approaches

Invasive approaches can be implemented by direct intraventricular injection in the brain, intracerebral injection or intrathecal infusion of the active substance, or by disruption of the BBB/BSCB (temporary rupture of the integrity of these barriers).

The principal problem of neurosurgical approaches by intraventricular injection, apart from the costs relating to the neurosurgical procedure, is that the drug is not delivered directly in the brain parenchyma but in the cerebrospinal fluid. Intraventricular infusion involves placing a catheter in the ventricles (Aird, 1984, *Exp. Neurol.*, 86, 342-358). This highly invasive technique is not effective for the transport of active substances in the nervous parenchyma. Indeed, in the brain for example, the flow volume from the cerebrospinal fluid to the brain parenchyma during delivery of a drug by intraventricular infusion is governed by an abnormally slow diffusion of its convection (transport), because the brain does not have intraparenchymal volumetric flow.

Similarly for intracerebral injection, the diffusion of an active substance in the brain decreases very quickly from the injection site to the site of the lesion. Indeed, the cerebral concentration of an active substance decreases by 90% at a distance of 500 μm from its injection site.

Intrathecal infusion involves placing a catheter in the brain. This catheter is connected to a pump that delivers the active substance at a predefined flow rate. Owing to the fact that the brain is the only organ that does not have a lymphatic system, normally serving to transport extracellular fluids back to general circulation, the distribution of an active substance by intrathecal infusion in the brain is very slow. This decreases the concentration of the active substance at the site of the lesion.

Moreover, risks of infection are significant during such neurosurgical procedures, notably by the presence of the catheter. Under these conditions, patient comfort is not optimal.

The temporary opening of the BBB is associated with transitory opening of the TJ of BCECs. This is the case for vasoactive substances such as leukotrienes or bradykinins (Baba et al., 1991, *J. Cereb. Blood Flow Metab.*, 11, 638-643). This strategy is equally invasive and requires arterial access to the carotid in sedated subjects/patients. The major problem encountered by the temporary rupture of the integrity of the BBB, besides expenses relating to the radiological procedure for access to the carotid, is that the BBB only remains open for a short period of time, thus limiting the possibility of delivering a drug over an extended period. Moreover, the temporary rupture of the BBB allows plasma proteins to enter the brain (whereas these proteins can be toxic for the brain) and can also facilitate the entry of infectious agents. This type of rupture of the BBB can thus lead to chronic neuropathologic disruptions and is associated with high risks of infection (Salahuddin et al., 1988, *Acta Neuropathol.*, 76, 1-10).

Pharmacological Approaches to Vectorization

Pharmacological strategies for transporting molecules include transcellular diffusion of molecules made more hydrophobic by the addition of lipid or lipophilic groups on the active substance (transcellular lipophilic diffusion, TLD) or the use of liposomes (Zhou et al., 1992, *J. Control. Release*, 19, 459-486), and transport by ionic adsorption via positively charged vector molecules or by cationization of the active molecule (adsorptive-mediated transport or AMT).

The addition of a lipid or lipophilic group enables the chemical conversion of hydrophilic molecules into more hydrophobic molecules notably through prodrug approaches. However, the synthesis of such compounds leads to molecules that exceed the optimal transport threshold to cross the BBB/BSCB/BRB, notably with regard to molecular weight (MW) which becomes greater than the optimal limit of 450 Daltons (Pajouhesh et al., 2005, *NeuroRx*, 2(4), 541-553). For the same reason, liposomes or even small vesicles (micelles, etc.) or nanoparticles (nanospheres, nanocapsules) are generally too large, are not specific enough for the BBB/BSCB/BRB, and consequently are relatively less effective for transporting molecules of therapeutic interest (or imaging or diagnostic agents, or any other molecule such as a molecular probe) across these barriers (Levin, 1980, *J. Med. Chem.*, 23, 682-684; Schackert et al., 1989, *Selective Cancer Ther.*, 5, 73-79). Moreover, this type of vesicle system generally has non-negligible toxic effects in the cerebrum. Thus, the principal problems encountered by lipidization technologies are their low specificity for specifically targeting and crossing the BBB/BSCB/BRB compared to other cell membranes, the decrease in the plasma values of the area under the curve (AUC) of the drug, and their generally limited use for vectorization of small molecules.

In AMT (addition of a cationic group via covalent bonding or direct cationization of the drug), the principal problem encountered is the low specificity for targeting and crossing specifically the BBB/BSCB/BRB compared to other cell membranes. Indeed, AMT is based on cationic molecules adsorbing on cells whose membrane is negatively charged, which is the case for most cells. The decrease in plasma values of the AUC of the drug, their generally limited use for vectorization of small molecules, and their cytotoxicity are additional factors which penalize the AMT vectorization approach.

Physiological Approaches to Vectorization

Strategies based on physiological approaches to vectorization consist in exploiting the various natural transport mechanisms of the barriers. These mechanisms of active transport of molecules across the BBB work either via coupling with a specific receptor substrate or by molecular mimicry with a specific receptor substrate (carrier-mediated transport or CMT), or via coupling or fusion with a ligand specifically targeting a receptor (receptor-mediated transport or RMT).

As an example, molecules such as L-DOPA (Parkinson's disease), melphalan (brain cancer), α-methyl-DOPA (arterial hypertension) and gabapentin (epilepsy) pass into the brain by CMT via large neutral amino-acid transporters 1 and 2 (LAT1 and LAT2), (Pardridge, 2003, *Mol. Interv.*, 3, 90-105). These molecules have chemical structures close to phenylalanine, one of the natural substrates of LAT1. However, the principal problems encountered by CMT approaches are their broad selectivity/specificity for conjugates that closely imitate/mimic the substrate of the endogenous receptor/transporter, and consequently their use which remains limited to vectorization of small molecules.

RMT calls upon a receptor-dependent transport system. Vectorization is carried out via mechanisms of endocytosis by targeting the endogenous receptors/transporters present in brain capillaries. Notable examples of the various human BBB receptors which would be involved in RMT include: transferrin receptor (TfR) which transports transferrin (Tf) bound to iron, insulin receptor (IR) or insulin-like growth factor receptor (IGFR), receptors which enable the transport of cholesterol contained in low density, high density, and very low density lipoproteins (LDL, HDL et VLDL respectively), including low-density lipoprotein (LDL) receptor and members of the family of low-density lipoprotein receptor-related protein (LRP), diphtheria toxin receptor (DTR) or heparin binding epidermal growth factor-like growth factor (HB-EGF), as well as scavenger receptors (SCAV-Rs) including scavenger receptor class B type I (SR-BI). In RMT, the receptors on the membrane of a BBB endothelial cell bind their ligand, which leads to endocytosis of the complex composed of the receptor/transporter and its ligand in a vesicle which forms on the cell surface and then penetrates the BBB endothelial cell. The ligand/receptor complex can pass through the endothelial cell (transcytosis), and can thus cross barriers such as BBB/BSCB/BRB to act in nervous tissue. This RMT process does not appear to depend on the size of the molecule engulfed by endocytosis. Thus, RMT is a mechanism that enables transport from the blood to the CNS or eye of many molecules or molecular complexes. Receptors for these molecules or molecular complexes can be used to transport the natural ligands of these receptors modified to carry drugs, and/or nanoparticles. For example, coating of nanoparticles with polysorbates, especially polysorbate 80 leads to the adsorption of apolipoprotein E from blood plasma onto the nanoparticle surface which then mimic low density lipoprotein (LDL) particles and could interact with the LDLR leading to their uptake by the endothelial cells (Kreuter, 2012, *Adv Drug Deliv Rev. pii: S0169-409X(12)00275-X*). LDL receptor-targeted liposome-encapsulated doxorubicin increases the in vitro drug delivery across BBB cells (Pinzon-Daza et al., 2012, *Br J. Pharmacol.* doi: 10.1111/j.1476-5381.2012.02103.x). Tf is the natural ligand of the TfR present on the BBB. Active substances have been coupled/conjugated to Tf for active transport across the BBB by the Tfr (Jefferies et al., 1984, *Nature*, 312, 162-163; Friden et al., 1983, *Science*, 259, 373-377; Friden, 1994, *Neurosurgery*, 35, 294-298). Although this vectorization strategy using a protein-type macromolecule enables an increase in the passage of the conjugate molecules of interest across the barriers, it has several disadvantages. First, the molecule is generally coupled/conjugated to the vector by gene expression methods (fusion) thus limiting the number of molecules to be transported to only polypeptides or proteins. Second, the system for coupling/conjugating the molecule with the vector is rather complex; traditional chemical or biochemical coupling does not yield well-defined macromolecular systems from a structural and molecular point of view. Moreover, potential competition between the conjugates and the endogenous ligands for the targeted receptor can lead either to an inhibition of the physiological process of RMT or to a decrease in the concentration of the endogenous ligands required for the proper functioning of the brain. Finally, RMT receptors are also involved in cell signaling processes in the cerebrum and the conjugates could potentially interfere with these processes.

RMT via specific receptors can also be used to target drugs into other tissues/organs than the BBB and the brain. Indeed, the vascular system of organs, the parenchyma of specific organs, or diseased tissues can express high levels of a given receptor which can be used for drug targeting (reviewed in Chung and Wasan, 2004, *Adv Drug Deliv Rev.* 2004 May 7; 56(9):1315-34). The LDLR for instance is expressed at high levels in the liver (in particular in the sinusoidal side of hepatocytes) and in other tissues such as the adrenal gland and intestine (Beisiegel et al., 1981, *J Biol. Chem.* 25; 256(8): 4071-8; Huettinger et al., 1984, *J Clin Invest.;* 74(3): 1017-26; Fong et al., 1989, *J Clin Invest;* 84(3): 847-56).

It has also been shown that uptake of cholesterol by the retina occurs primarily via a LDLR-mediated process (Tserentsoodol et al., 2006, *Molecular Vision* 2006; 12:1306-18). Finally, there is ample evidence for LDLR increased expression in numerous types of cancers and for LDL- or nanoparticule-mediated anticancer drug delivery via these LDLR of cancer cells including glioblastoma (Varshosaz et al., 2012, *Eur J Med Chem;* 54:429-38; Kopecka et al., 2011; *Journal of Controlled Release;* 149:196-205; Nikanjam et al., 2007, *Int J. Pharm.;* 328(1): 86-94; reviewed in Ng et al., 2011, *Acc Chem Res;* 44(10):1105-13; Firestone, 1994, *Bioconjug Chem.;* 5(2):105-13.).

It has also been shown that several LDLR endogenous ligands such as LDLs or PCSK9, after binding to LDLR, undergo receptor-mediated-endocytosis followed by intracellular trafficking of membrane vesicles (endosomes) that ultimately fuse with lysosomes (Issandou et al., 2004, *Bio-*

*chem Pharmacol.;* 67(12):2281-9; reviewed in Lambert et al., 2009, *Atherosclerosis.;* 203(1): 1-7).

Lysosomal Storage Diseases (LSD) represent about 70 genetically distinct conditions, with a combined birth frequency of about 1 in 7500. Enzyme replacement therapies (ERT) require uptake of the recombinant enzymes considered for treatment of the multiple LSD. The mannose-phosphate receptor (M6PR) is currently a major target for enzyme delivery to tissues and to the lysosomal compartment of cells (Reviewed in Cox, 2012, *J Pathol.;* 226(2):241-54; Lachmann, 2011, *Curr Opin Pediatr.;* 23(6): 588-93), but other receptors, such as those involved in RMT could be considered, in particular for targeting ERT to the CNS, considering that approximately ⅔ of LSD affect the CNS.

International patent application WO2010/046588 describes for the first time peptides or pseudo-peptides that bind human, mice or rat LDLR and are able to carry across the BBB substances that can be of high MW and/or large volume.

The present application relates to novel peptides that bind LDLR, particularly human, mice and/or rat LDLR, and which are optimized for addressing molecules towards LDLR-expressing tissues, healthy or pathologic, and in particular across the physiological barriers of the nervous system such as the BBB, BSCB or BRB.

SUMMARY OF THE INVENTION

The present invention provides optimized peptides or pseudo-peptides capable of transporting across cell membranes of LDLR-expressing tissues, and in particular across physiological barriers of the CNS or retina (BBB/BSCB and BRB), substances that can be of high MW and/or large volume. The invention thus makes it possible to improve the biodistribution or the bioavailability of molecules of interest, and notably to improve their access (targeting) to the CNS and/or the eye and/or other organs enriched in LDLR, and/or towards different cancer cells enriched in LDLR, and/or towards lysosomal compartments of cells.

In application WO2010/046588, the inventors have developed peptide derivatives capable of binding LDLR. The inventors have shown that these derivatives are capable of crossing the BBB. The inventors have also shown that these derivatives can address to the brain molecules, including molecules of therapeutic or diagnostic interest.

Continuing their research, the inventors succeeded in designing and testing novel peptides exhibiting advantageous properties for the transport of molecules. These novel peptides, capable of binding LDLR without competition with the natural ligand, and thus without interference with the transport of endogenous LDL, represent novel products (vectors) that are particularly advantageous for the design and vectorization of diagnostic or imaging drugs or agents, notably to reach the CNS. Depending on their properties, these peptides allow the targeting of molecules towards the CNS and/or the eye and/or other organs enriched in LDLR (e.g., liver, adrenal gland, intestine), and/or towards cancer cells enriched in LDLR, and/or towards lysosomal compartments of cells.

One object of the invention is thus a peptide or pseudo-peptide, characterized in that it is of the following general formula (I):

A1-Met-A2-Arg-Leu-Arg-A3-A4 (I)

wherein A1 and A4 independently represent cysteine or an analogue thereof or an isostere thereof, A2 represents proline or an analogue thereof or an isostere thereof, and A3 represents glycine or an analogue thereof or an isostere thereof.

According to preferred embodiments, A1 represents cysteine (Cys) or an analogue thereof selected from (D)-cysteine, penicillamine (Pen) and (D)-penicillamine ((D)-Pen); A2 represents proline (Pro) or an analogue thereof selected from pipecolic acid (Pip) and thiazolidine-4-carboxylic acid (Thz); and/or A3 represents glycine (Gly), or sarcosine (Sar) and/or A4 represents cysteine or an analogue thereof selected from (D)-cysteine, Penicillamine (Pen), and (D)-Penicillamine ((D)-Pen).

A preferred object of the invention is a peptide or pseudo-peptide of the following general formula (I'):

A1-Met-A2-Arg-Leu-Arg-Gly-A4 (I')

wherein A1 represents cysteine or an analogue thereof preferably selected from (D)-cys, Pen and (D)-Pen; and A2 represents proline or an analogue thereof preferably selected from Pip and Thz; and/or A4 represents cysteine or an analogue thereof selected from (D)-cysteine, Penicillamine (Pen), and (D)-Penicillamine ((D)-Pen).

Another particular object of the invention is a peptide or pseudo-peptide of the following general formula (I'):

A1-Met-A2-Arg-Leu-Arg-Ala-A4 (I')

wherein A1 represents cysteine or an analogue thereof preferably selected from (D)-cys, Pen and (D)-Pen; and A2 represents proline or an analogue thereof preferably selected from Pip and Thz; and/or A4 represents cysteine or an analogue thereof selected from (D)-cysteine, Penicillamine (Pen), and (D)-Penicillamine ((D)-Pen). The alanine (Ala) can be of L or D configuration.

In a preferred embodiment, A4 is Cys.

The peptides of the invention advantageously have the ability to bind human LDL receptor (hLDLR), mice LDLR, or rat LDLR. Furthermore, they are small, typically fewer than 10 amino acids, which is particularly advantageous. Particular examples of such peptides are peptides of sequences SEQ ID NOs: 1 to 10 and 26 to 30.

Another object of the invention relates to the use of a peptide or pseudo-peptide such as defined above for preparing a pharmaceutical or diagnostic composition to vectorize an active substance or a substance of diagnostic, imaging or therapeutic interest.

Another object of the invention relates to the use of a peptide or pseudo-peptide such as defined above for increasing the biological activity or for decreasing the toxicity of an active substance or of a substance of interest to which it is coupled.

Another object of the invention relates to a peptide or pseudo-peptide such as defined above for use to vectorize an active substance or a substance of diagnostic, imaging or therapeutic interest.

Another object of the invention relates to a peptide or pseudo-peptide such as defined above for use to increase the biological activity or to decrease the toxicity of an active substance or a substance of interest to which it is coupled.

Another object of the invention relates to any conjugated compound of the following formula (II):

VxDy (II)

wherein V represents a peptide or pseudo-peptide such as defined above, D represents an active substance or a substance of interest, and x and y are integers between 1 and 5.

The invention also relates to any conjugated compound of the following formula (III):

VxLzDy (III)

wherein V represents a peptide or pseudo-peptide such as defined above, L represents a spacer, D represents an active substance or a substance of interest, x and y are integers between 1 and 5 and z is an integer between 1 and 10.

Another object of the invention relates to a pharmaceutical composition containing at least one conjugated compound such as defined above and one or more pharmaceutically acceptable excipients.

Another object of the invention relates to a diagnostic composition characterized in that it contains a medical diagnostics or imaging agent comprised of a conjugated compound such as defined above.

Another object of the invention relates to a method for improving or enabling the passage of a molecule across cell membranes of LDLR-expressing tissues, healthy or pathologic, and in particular across the physiological barriers BBB/BSCB and BRB, comprising the coupling of said molecule to a peptide or pseudo-peptide such as defined above.

Another object of the invention is an improved method for treating with a drug a pathology in a subject, the improvement consisting in coupling said drug with a peptide or pseudo-peptide such as defined above.

The invention can be used in any mammal, in particular any human being.

BRIEF DESCRIPTION OF FIGURES

The patent or application file contains at least one drawing executed in color. Copies of this patent or patent application publication, with color drawing(s), will be provided by the Office upon request and payment of the necessary fee.

B—Pulse-chase experiment using CHO-hLDLR-GFP cells grown on coverslips and incubated with the peptide-STag conjugate (SEQ ID NO: 17). After 5 minutes incubation, cells are extensively washed and then incubated in chase media for 1 hour, fixed, permeabilized and stained using a lysosomal marker (LAMP1). Nuclei are stained using Hoechst. Insets show higher magnification of an area of confocal images corresponding to lysosomes. Note that most of the peptide staining colocalizes with lysosomes.

Figure 9:
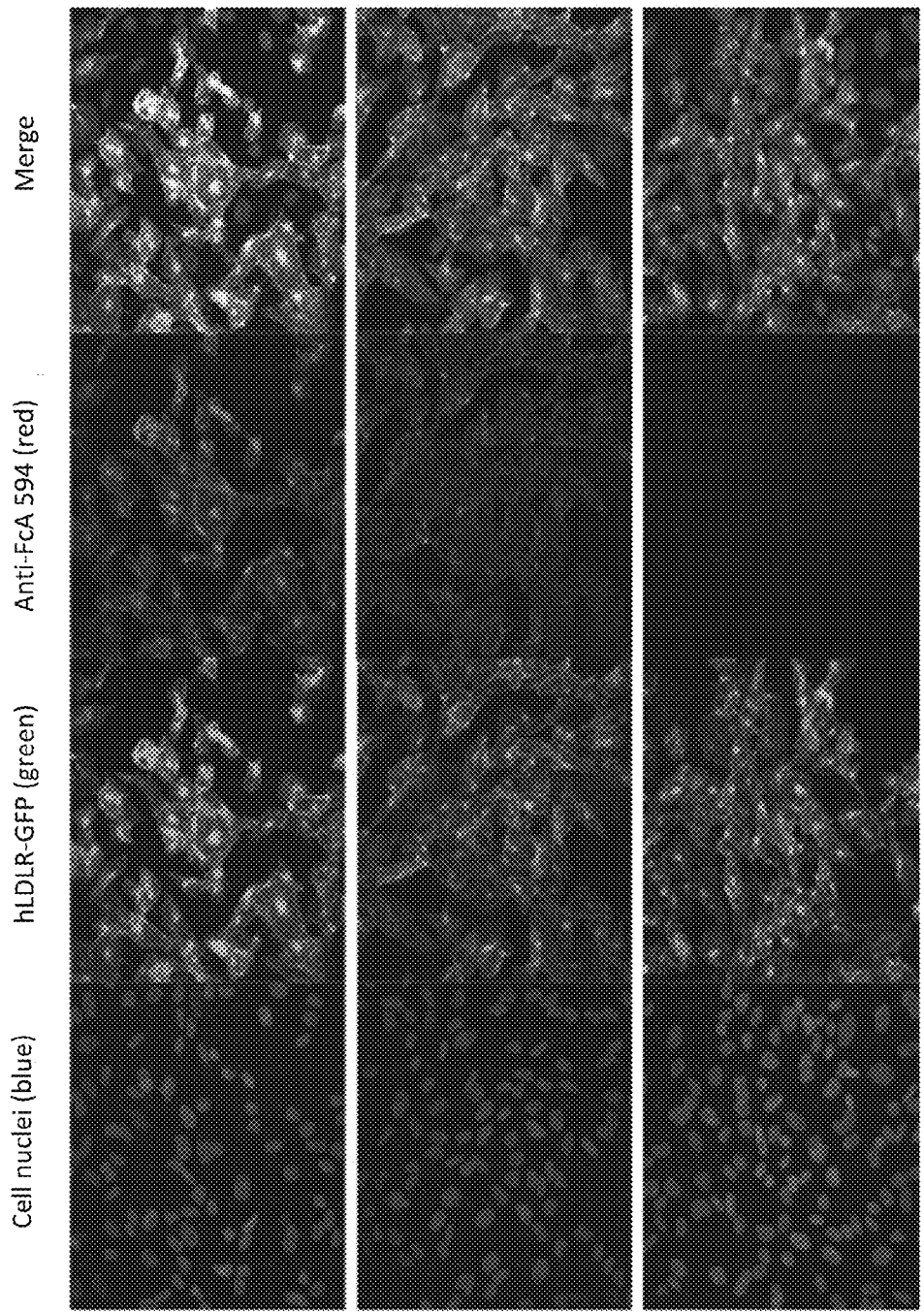
Figure 12A:
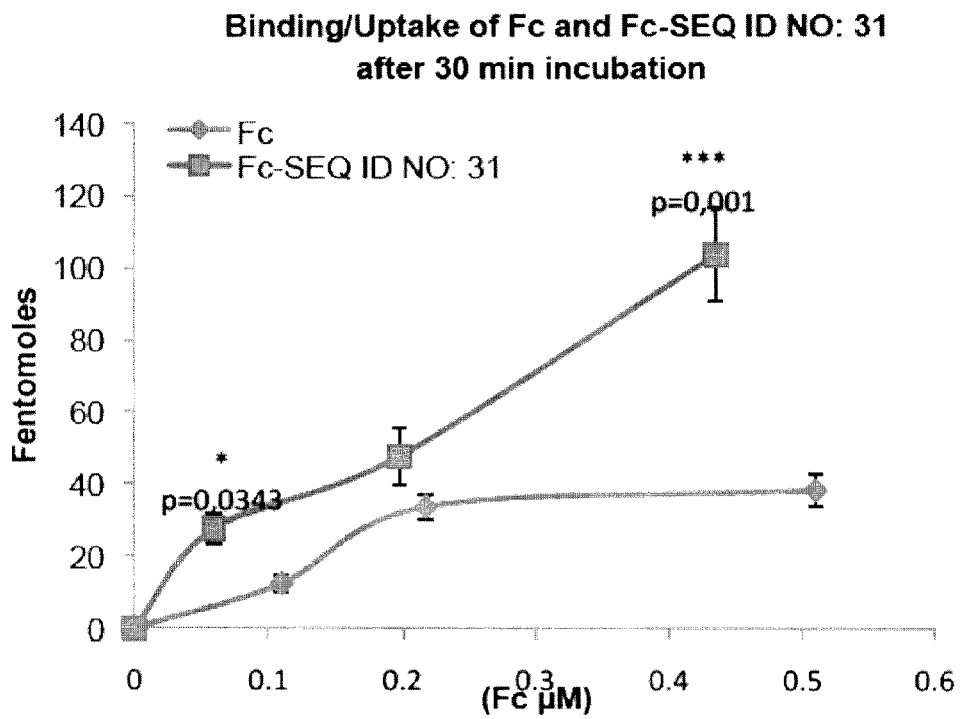
Figure 12B:
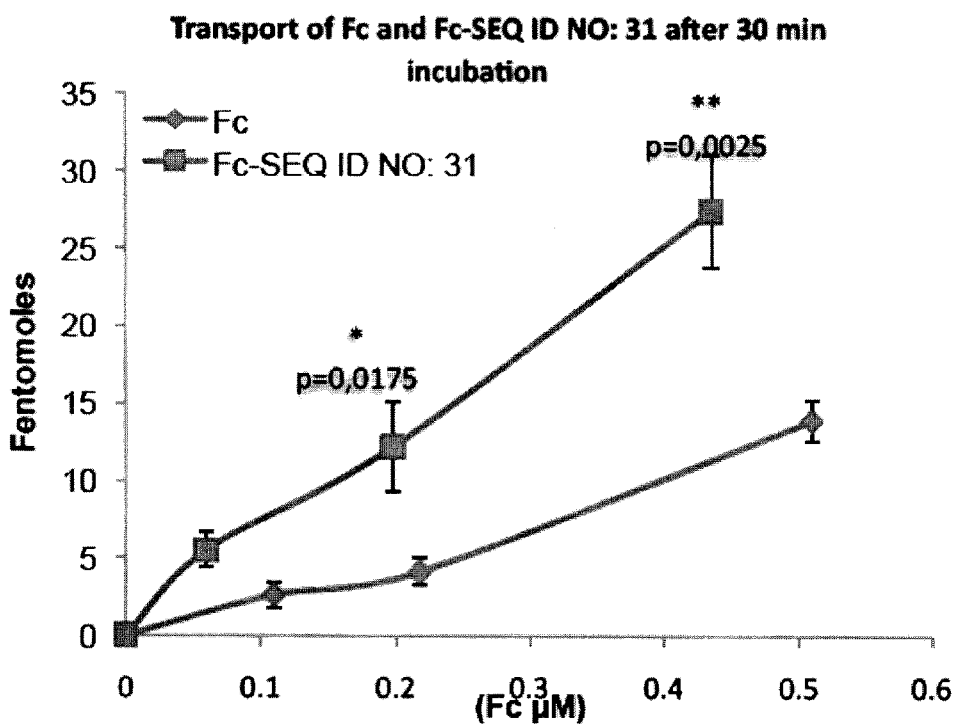
Figure 12C:
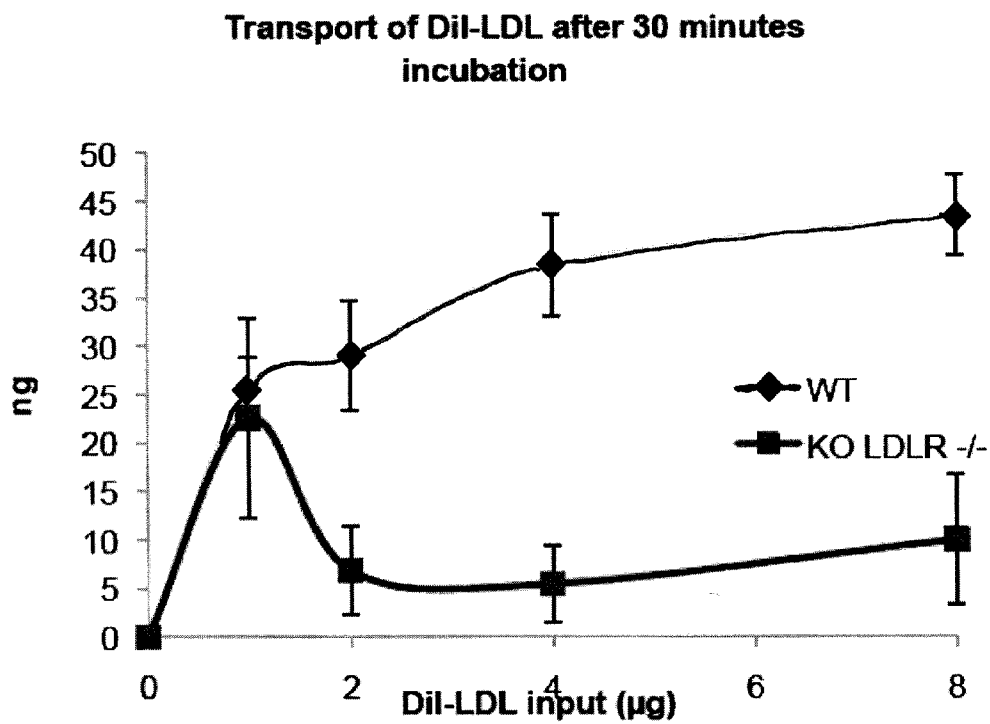
Figure 12D:
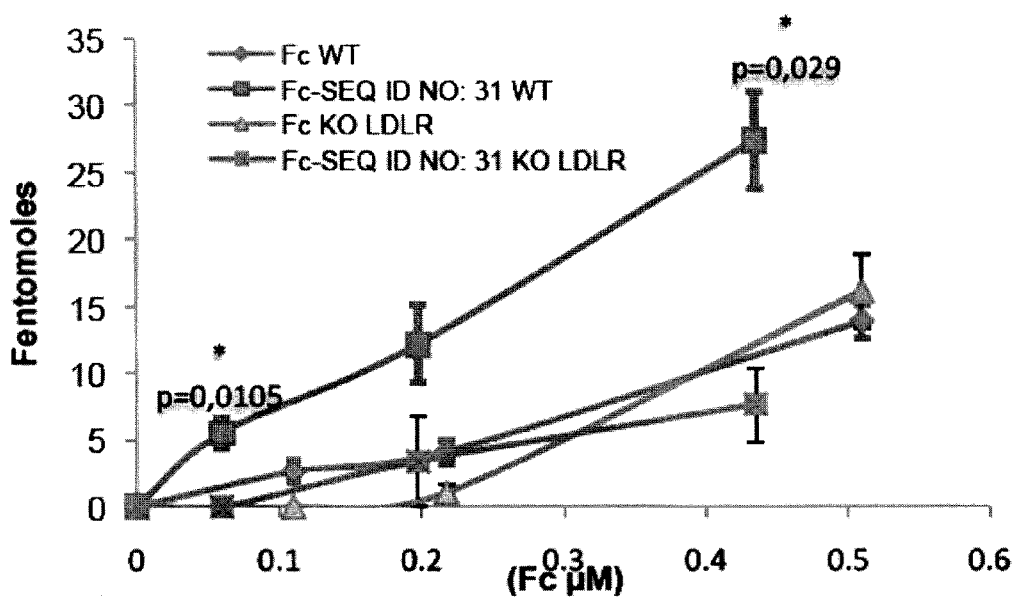

FIG. 9. Binding of the Fc-SEQ ID NO: 17 (chemically linked) and of the Fc-SEQ ID NO: 31 (fusion) to CHO hLDLR cells.

Comparison by immunocytochemistry of the binding of Fc-SEQ ID NO: 17 and of Fc-SEQ ID NO: 31 to hLDLR-GFP (green) expressed by CHO cells. 5 nM of the fusion or chemically-linked proteins or of Fc alone are incubated 1 h with cells before fixation. Cell nuclei are stained with Hoechst (blue). Fc is detected with an anti-human Fc antibody conjugated to Alexa 594 (red). The overlap of red and green stainings is visible in yellow/orange on merge. Note that only Fc-SEQ ID NO: 17 and of Fc-SEQ ID NO: 31 bind hLDLR. Arrows indicate colocalization.

FIG. 10. In vitro blood-brain barrier (BBB) model: rat brain capillary endothelial cells (RBCEC) co-cultured with astrocytes. In A, live RBCEC were incubated with DiI-LDL at 40 µg/mL during 30 min incubation. In B, rat LDLR labelling at the surface of live RBCEC with a goat antibody that recognizes the extracellular domain of Human mouse and rat LDLR (R&D Systems CAT No. AF2255) at 10 µg/mL during 1 h incubation. In C, the same antibody labels the rat RBCEC LDLR following fixation of cells with PFA 4%, without permeabilization.

Flow cytometry: Mechanical dissociation of the RBCEC monolayer with EDTA 0.25 mM. In E, control RBCEC labelled with phycoerythrin PE-A. In F, DiI-LDL binding on the LDLR receptors of the RBCEC, at 40 µg/mL during 90 min at 4° C. In G, RBCEC with secondary antibody only (donkey anti goat Allophycocyanin APC, used as control). In H, labelling with the goat anti LDLR(R&D systems) at 10 µg/mL during 45 min at 4° C., followed by secondary antibody.

FIG. 11. In vitro BBB model: rat brain capillary endothelial cells (RBCEC) co-cultured with astrocytes. A to F: incubations on live RBCEC from wild type (WT) rats, G and H: live RBCEC from LDLR −/− (KO) rats. In A, binding/uptake of Fc at 0.25 µM during 30 min incubation on live WT RBCEC. In B, binding/uptake of Fc-SEQ ID NO: 31 at 0.25 µM during 30 min incubation on live WT RBCEC. In C and E, binding/uptake of DiI-LDL at 40 µg/mL during 30 min incubation on live WT RBCEC. In D and F, binding/uptake of Fc-SEQ ID NO: 31 at 0.25 µM during 30 min incubation. E and F are the same photomicrographs as in C and D at a higher magnification. These photomicrographs show the colocalization between DiI-LDL and Fc-SEQ ID NO: 31. In G, binding/uptake of DiI-LDL at 40 µg/mL during 30 min incubation on live RBCEC from KO rats. In H, binding/uptake of Fc-SEQ ID NO: 31 at 0.25 µM during 30 min incubation on live RBCEC from KO rats.

FIG. 12. In vitro BBB model: rat brain endothelial cells (RBCEC) co-cultured with astrocytes.

In A, binding/uptake of Fc and Fc-SEQ ID NO: 31 at different concentrations after 30 min incubation on live WT RBCEC. In B, transport across the RBEC monolayer into the lower compartment of Fc and Fc-SEQ ID NO: 31 at different concentrations after 30 min incubation on live WT RBCEC. In C, transport in the lower compartment of DiI-LDL at different concentrations after 30 min incubation on live WT and KO RBCEC. In D, transport in the lower compartment of Fc and Fc-SEQ ID NO: 31 at different concentrations after 30 min incubation on live WT and KO RBCEC.

DETAILED DESCRIPTION OF THE INVENTION

The invention relates to peptide derivatives capable of binding human LDLR and the use thereof in the field of pharmaceuticals, notably to transport molecules of therapeutic or diagnostic interest across cell membranes of LDLR-expressing tissues, healthy or pathologic, and in particular across the physiological barriers BBB/BSCB and BRB.

Human LDLR is a transmembrane protein of 839 amino acids comprising three regions: the extracellular region (1-768), the transmembrane region (768-790) and the cytoplasmic region (790-839). The extracellular region is divided into two subregions: that of LDL binding (1-322) and that outside the LDL binding region (322-768) (see WO2007/014992).

The brain uses cholesterol for its proper functioning. Cholesterol is produced endogenously and is also transported in the blood stream by LDLs, a lipoproteic complex enriched in cholesterol associated with apolipoprotein B (ApoB) and captured in tissues notably by the LDLR, which thus enables the transport of cholesterol across cell membranes.

It has been shown that LDLR enabled the transcytosis of LDL particles across the BBB (Dehouck et al., 1997, *J. Cell Biol.,* 138(4), 877-889), via an RMT process, in specific endosomal vesicles that prevent fusion with the lysosome. These lipoproteins, having crossed the BBB by transcytosis, are then taken up by neurons and/or astrocytes (Spencer et al., 2007, *Proc. Natl. Acad. Sci. USA,* 104(18), 7594-7599). This property was used to vectorize molecules of therapeutic interest by nanoparticles conjugated to apolipoproteins in order to mimic LDL particle structure (Kreuter et al., 2007, *J. Control. Release,* 118, 54-58).

International patent application No WO2010/046588 describes for the first time peptides or pseudo-peptides that bind human LDLR and are able to carry across the BBB substances that can be of high MW and/or large volume.

The present application relates to novel peptides binding human LDLR, optimized for the transport of molecules. Peptide or pseudo-peptide vectors can be easily synthesized chemically, and many molecules of therapeutic interest or imaging or diagnostic agents can be coupled with peptide or pseudo-peptide vectors simply and effectively through a prodrug strategy via a spacer (synthesis via a linker) or by direct coupling (synthesis in tandem) between the two entities (FIG. 2). The inventive peptides and pseudo-peptides are designed to adopt a cyclic configuration, thus more resistant to proteolysis. Moreover, the inventive peptides and pseudo-peptides bind LDLR without competition with the natural ligand.

The peptides or pseudo-peptides of the invention can be used as vectors for molecules of therapeutic interest, or for imaging or diagnostic agents, or for any other molecule such as a molecular probe, in the treatment, imaging and/or diagnosis of neurological pathologies, as well as genetic, infectious, inflammatory, or cancerous pathologies of the brain or other tissues.

The peptides or pseudo-peptides described in the present invention have the capacity to target cell receptors/transporters and particular cell types and/or to cross cell membranes, notably those of the physiological barriers of the brain and more particularly the BBB/BSCB or BRB.

The peptides or pseudo-peptides described in the present invention have the capacity to target cell receptors/transporters and particular cell types, notably cancer cells, nervous or non-nervous tissues and/or to cross cell membranes, notably those of the physiological barriers of the nervous system and more particularly of the CNS and retina, particularly the BBB, BSCB, BRB, or the blood-tumor barrier (BTB) of cancerous nervous tissue tumors.

The peptides or pseudo-peptides described in the present invention have the capacity to target cell receptors/transporters and particular cell types and/or to cross cell membranes, notably those of the physiological barriers of the CNS, to treat more particularly infectious brain pathologies or other pathologies of a bacterial, viral, parasitic or fungal nature/origin.

The peptides or pseudo-peptides described in the present invention have the capacity to bind to human, mouse and/or rat LDLR of the cell membranes and to cross the aforesaid membranes via this receptor by endocytosis.

The peptides or pseudo-peptides described in the present invention have the capacity to bind to LDLR at the surface of cell membranes of physiological barriers of the human, mouse and/or rat CNS or eye and to cross the aforesaid physiological barriers via LDLR by receptor mediated transport/transcytosis (RMT).

One object of the invention thus relates to peptides or pseudo-peptides, characterized in that they are of the following general formula (I):

A1-Met-A2-Arg-Leu-Arg-A3-A4 (I)

wherein:

- A1 represents cysteine or an analogue thereof or an isostere thereof,
- A2 represents proline or an analogue thereof or an isostere thereof,
- A3 represents glycine or an analogue thereof or an isostere thereof, and
- A4 represents cysteine or an analogue thereof or an isostere thereof.

More particularly, group A1 represents a residue selected from cysteine (Cys, C), of D or L configuration, or a derivative thereof selected from 2-amino-3-mercaptopropanoic acid and S-substituted derivatives thereof, S-acetylcysteine or 2-amino-3-(acetylthio)propanoic acid, selenocysteine (Sec, U) or 2-amino-3-(seleno)propanoic acid, cysteinol, 3-mercaptopropanoic acid (Mpa) or penicillamine (Pen), of L or D configuration.

Group A2 represents more preferentially a residue selected from proline (Pro, P) or pyrrolidine-2-carboxylic acid, homoproline or 2-(2-pyrrolidinyl)ethanoic acid, 3-hydroxyproline (3Hyp), 4-hydroxyproline (4Hyp), 3-methylproline, 3,4-dehydroproline, 3,4-methanoproline, 4-aminoproline, 4-oxoproline, thioproline or thiazolidine-4-carboxylic acid (Thz), 2-oxothiazolidine-4-carboxylic acid, indolin-2-carboxylic acid (Idc), pipecolic acid (Pip) or piperidin-2-carboxylic acid, nipecotic acid (Nip) or piperidin-3-carboxylic acid, 4-oxopipecolic acid, 4-hydroxypipecolic acid, amino-1-cyclohexanecarboxylic acid, prolinol. In a preferred embodiment, group A2 is selected from Pro, Pip or Thz.

Group A3 represents more preferentially a residue selected from glycine (Gly, G) or 2-aminoethanoic acid, sarcosine (Sar) or N-methylglycine (MeGly), N-ethylglycine (EtGly), allylglycine (allylGly) or 2-aminopent-4-enoic acid, 2-cyclopentylglycine (Cpg), 2-cyclohexylglycine (Chg), 2,2-dipropylglycine (Dpg), 2-(3-indolyl)glycine (IndGly), 2-indanylglycine (Igl), 2-neopentylglycine (NptGly), 2-octylglycine (OctGly), 2-propargylglycine (Pra) or 2-amino pent-4-ynoic acid, 2-phenylglycine (Phg), 2-(4-chlorophenyl)glycine, azaglycine (AzGly), or glycinol or 2-aminoethanol.

In a preferred embodiment, group A3 is selected from Gly and Sar.

Group A4 represents a residue selected from cysteine (Cys, C), of D or L configuration, or a derivative thereof selected from 2-amino-3-mercaptopropanoic acid and S-substituted derivatives thereof, S-acetylcysteine or 2-amino-3-(acetylthio)propanoic acid, selenocysteine (Sec, U) or 2-amino-3-(seleno)propanoic acid, cysteinol, or penicillamine (Pen), of L or D configuration. In a preferred embodiment, group A4 is selected from Cys or Pen, of L or D configuration. In a most preferred embodiment, A4 is Cys.

Among the peptides or pseudo-peptides of formula (I), particularly preferable are the peptides in which group A3 is Gly. Thus, a particular object of the invention relates to peptides of the following formula (I'):

A1-Met-A2-Arg-Leu-Arg-Gly-A4    (I')

wherein A1 represents cysteine or an analogue thereof or an isostere thereof, preferably A1 represents Cys, (D)-cys, Pen, or (D)-Pen; A2 represents a proline analogue, preferably A2 represents Pip or Thz, and A4 represents Cys or an analogue thereof or an isostere thereof, preferably A4 represents Cys, (D)-Cys, Pen, or (D)-Pen.

Particular examples of peptides according to the invention are described below:

SEQ ID NO: 1, (D)-cys-Met-Pip-Arg-Leu-Arg-Gly-Cys;

SEQ ID NO: 2, (D)-pen-Met-Pip-Arg-Leu-Arg-Gly-Cys;

SEQ ID NO: 3, Pen-Met-Pip-Arg-Leu-Arg-Gly-Cys;

SEQ ID NO: 4, (D)-cys-Met-Thz-Arg-Leu-Arg-Gly-Cys;

SEQ ID NO: 5, (D)-pen-Met-Thz-Arg-Leu-Arg-Gly-Cys;

SEQ ID NO: 6, Pen-Met-Thz-Arg-Leu-Arg-Gly-Cys;

SEQ ID NO: 7, (D)-cys-Met-Thz-Arg-Leu-Arg-Sar-Cys;

SEQ ID NO: 8, (D)-pen-Met-Thz-Arg-Leu-Arg-Sar-Cys;

SEQ ID NO: 9, Pen-Met-Thz-Arg-Leu-Arg-Sar-Cys;

SEQ ID NO: 10, (D)-cys-Met-Pro-Arg-Leu-Arg-(D)-ala-Cys;

SEQ ID NO: 26, (D)-Cys-Met-Thz-Arg-Leu-Arg-Gly-Pen;

SEQ ID NO: 27, (D)-Cys-Met-Thz-Arg-Leu-Arg-Sar-Pen;

SEQ ID NO: 28, (D)-Cys-Met-Pip-Arg-Leu-Arg-Sar-Cys;

SEQ ID NO: 29, (D)-Cys-Met-Pip-Arg-Leu-Arg-Gly-Pen;

SEQ ID NO: 30, (D)-Cys-Met-Pip-Arg-Leu-Arg-Sar-Pen.

The results obtained by the applicant show that the peptides of the invention have an improved affinity for LDLR. Thus, compared to the reference peptide SEQ ID NO: 17, all the peptides of formula (I) tested exhibit improved affinity, as seen in Table 1 (EXAMPLE III). These results are all the more remarkable as the modification of other residues in the sequence, such as for example the replacement of arginine residues, led to a substantial drop in affinity (see reference peptides SEQ ID NO: 11-16).

SEQ ID NO: 11, (D)-Cys-Met-Pro-hArg-Leu-Arg-Gly-Cys;

SEQ ID NO: 12, (D)-Cys-Met-Pro-Agb-Leu-Arg-Gly-Cys;

SEQ ID NO: 13, (D)-Cys-Met-Pro-Agp-Leu-Arg-Gly-Cys;

SEQ ID NO: 14, (D)-Cys-Met-Pro-Cit-Leu-Arg-Gly-Cys;

SEQ ID NO: 15, (D)-Cys-Met-Pro-Arg-Leu-Cit-Gly-Cys;

SEQ ID NO: 16, (D)-Cys-Met-Pro-Arg-Leu-Arg(NO2)-Gly-Cys;

SEQ ID NO: 17, (D)-Cys-Met-Pro-Arg-Leu-Arg-Gly-Cys;

SEQ ID NO: 31, Cys-Met-Pro-Arg-Leu-Arg-Gly-Cys.

These results are also particularly remarkable taking into account the small size of the peptides (the peptides above contain 8 amino acids), which constitutes an additional advantage in their industrial use.

As indicated above, the cyclic peptides or pseudo-peptides of the invention can comprise peptide, non-peptide and/or modified peptide bonds. In a preferred embodiment, the peptides or pseudo-peptides comprise at least one peptidomimetic bond, chosen preferably among intercalation of a methylene (—$CH_2$—) or phosphate (—$PO_2$—) group, secondary amine (—NH—) or oxygen (—O—), alpha-azapeptides, alpha-alkylpeptides, N-alkylpeptides, phosphonamidates, depsipeptides, hydroxymethylenes, hydroxyethylenes, dihydroxyethylenes, hydroxyethylamines, retro-inverso peptides, methyleneoxy, cetomethylene, esters, phosphinates, phosphinics, phosphonamides and carba analogues.

Furthermore, in a particular embodiment, the peptides or pseudo-peptides of the invention comprise an N-term and/or C-term function respectively protected, for example, by acylation, or amidation or esterification.

The peptides or pseudo-peptides of the invention can be synthesized by any technique known to those persons skilled in the art (chemical, biological or genetic synthesis, etc.).

They can be preserved as-is, or be formulated in the presence of a substance of interest or any acceptable excipient.

For chemical syntheses, commercial apparatuses that can incorporate natural as well as non-natural amino acids, such as D enantiomers and residues with side chains with hydrophobicities and steric obstructions different from those of their natural homologues (so-called exotic, i.e., non-coded, amino acids), or a peptide sequence containing one or more peptidomimetic bonds that can include notably intercalation of a methylene (—CH$_2$—) or phosphate (—PO$_2$—) group, a secondary amine (—NH—) or an oxygen (—O—) or an N-alkylpeptide, are used.

During synthesis, it is possible to introduce various chemical modifications, such as for example, putting in the N-term or C-term position or on a side chain a lipid (or phospholipid) derivative or a constituent of a liposome or a nanoparticle, in order to be able to incorporate the peptide or pseudo-peptide of the invention within a lipid membrane such as that of a liposome composed of one or more lipid layers or bilayers, or of a nanoparticle.

The peptides of the invention, or a proteic part thereof, can also be obtained from a nucleic acid sequence coding for the same. The present invention also relates to a nucleic acid molecule comprising, or consisting of, a nucleic acid sequence coding for a peptide such as defined above. More particularly, the invention relates to a nucleic acid molecule comprising at least one sequence coding for a peptide of general formula (I). These nucleic acid sequences can be DNA or RNA and be combined with control sequences and/or be inserted in biological expression vectors.

The biological expression vector used is selected according to the host in which it will be transferred. It can be, for example, a plasmid, cosmid, virus, etc. The invention relates in particular to these nucleic acids and biological expression vectors, which can be used to produce the peptides of the invention, or proteic parts thereof, in a host cell. These biological expression vectors can be prepared and the peptides can be produced or expressed in a host by molecular biology and genetic engineering techniques well known to those persons skilled in the art.

Another object of the invention relates to the use of a cyclic peptide or pseudo-peptide such as defined above, as a vector for the transfer/transport of molecules of therapeutic interest, or of imaging or diagnostic agents, or of any other molecule.

The invention also relates to the use of a cyclic peptide or pseudo-peptide such as defined above for preparing a medicament capable of crossing cell membranes of LDLR-expressing tissues, healthy or pathologic, the and in particular across the physiological barrier BBB/BSCB and BRB.

The invention also relates to a method for enabling or improving the passage of a molecule across cell membranes of LDLR-expressing tissues, healthy or pathologic, and in particular across the physiological barriers BBB/BSCB and BRB, comprising the coupling of the molecule to a peptide or pseudo-peptide of the invention.

Thus, the invention relates in particular to a conjugate compound of formula (II) as follows:

VxDy                                         (II)

wherein V represents a peptide or pseudo-peptide of the invention, D represents an active substance or a substance of interest, and x and y are integers between 1 and 5. In a particular embodiment, x and y are equal to 1, x is greater than y, or y is greater than x.

The invention also relates to a conjugate compound of formula (III) as follows:

VxLzDy                                       (III)

wherein V represents a peptide or pseudo-peptide of the invention, L represents a spacer, D represents an active substance or a substance of interest, x and y are integers between 1 and 5 and z is an integer between 1 and 10. In a particular embodiment, x=z=y=1 or x=z>y or y=z>x or z>x>y.

The active substance or substance of interest can be any molecule of pharmaceutical interest, notably therapeutic, a diagnostic or medical imaging agent, or a molecular probe. It can be in particular any chemical entity of biological interest such as a small chemical molecule (antibiotic, antiviral, immunomodulator, antineoplastic, anti-inflammatory, etc.), a peptide or polypeptide, a protein (enzyme, notably lysosomal, hormone, cytokine, apolipoprotein, growth factor, antigen, antibody or part of an antibody), a nucleic acid (ribonucleic acid or deoxyribonucleic acid of human, viral, animal, eukaryotic or prokaryotic, plant or synthetic origin, etc., whose size can range from that of a single oligonucleotide to that of the genome or a genome fragment), a viral genome or a plasmid, a ribozyme, a marker or a tracer. Generally, the "substance of interest" can be any drug active ingredient, whether a chemical, biochemical, natural or synthetic compound. The expression "small chemical molecule" designates a molecule of pharmaceutical interest with a maximum molecular weight of 1000 Daltons, typically between 300 Daltons and 700 Daltons.

The invention also relates to a compound of following formula (IV):

VxLz                                         (IV)

wherein V represents a peptide or pseudo-peptide of the invention, L represents a spacer, x is an integer between 1 and 5 and z is an integer between 1 and 10. In a particular embodiment, x=z=1 or z>x.

In the conjugate compounds of the invention, coupling between V and D, or between V and L on the one hand and L and D on the other hand, can be carried out by any acceptable means of bonding taking into account the chemical nature, obstruction and number of associated active substances and peptides or pseudo-peptides. Coupling can thus be carried out by one or more covalent, ionic, hydrogen, hydrophobic or Van der Waals bonds, cleavable or non-cleavable in physiological medium or within cells. Furthermore, D can be coupled with V, if need be via L, at various reactive groups, and notably at one or more N-term and/or C-term ends of V and/or at one or more reactive groups carried by the natural or non-natural amino acid side chains constitutive of V.

Coupling can be carried out at any site of the peptide or pseudo-peptide where functional groups such as —OH, —SH, —CO$_2$H, —NH$_2$, —SO$_3$H or —PO$_2$H are naturally present or have been introduced. Thus, a therapeutic molecule of interest, or a diagnostic (or medical imaging) agent or any other molecule such as a molecular probe can be linked (coupled) to the peptide or pseudo-peptide vector by a covalent bond either at the N-term or C-term ends, or at the reactive groups carried by the natural or non-natural amino acid side chains of this peptide sequence.

Similarly, coupling can be carried out at any site of the active substance or substance of interest (molecule of therapeutic interest, diagnostic or medical imaging agent, any other molecule such as a molecular probe) where, for example, functional groups such as —OH, —SH, —CO$_2$H, —NH$_2$, —SO$_3$H, —PO$_2$H are naturally present or have been introduced.

Figure 1:
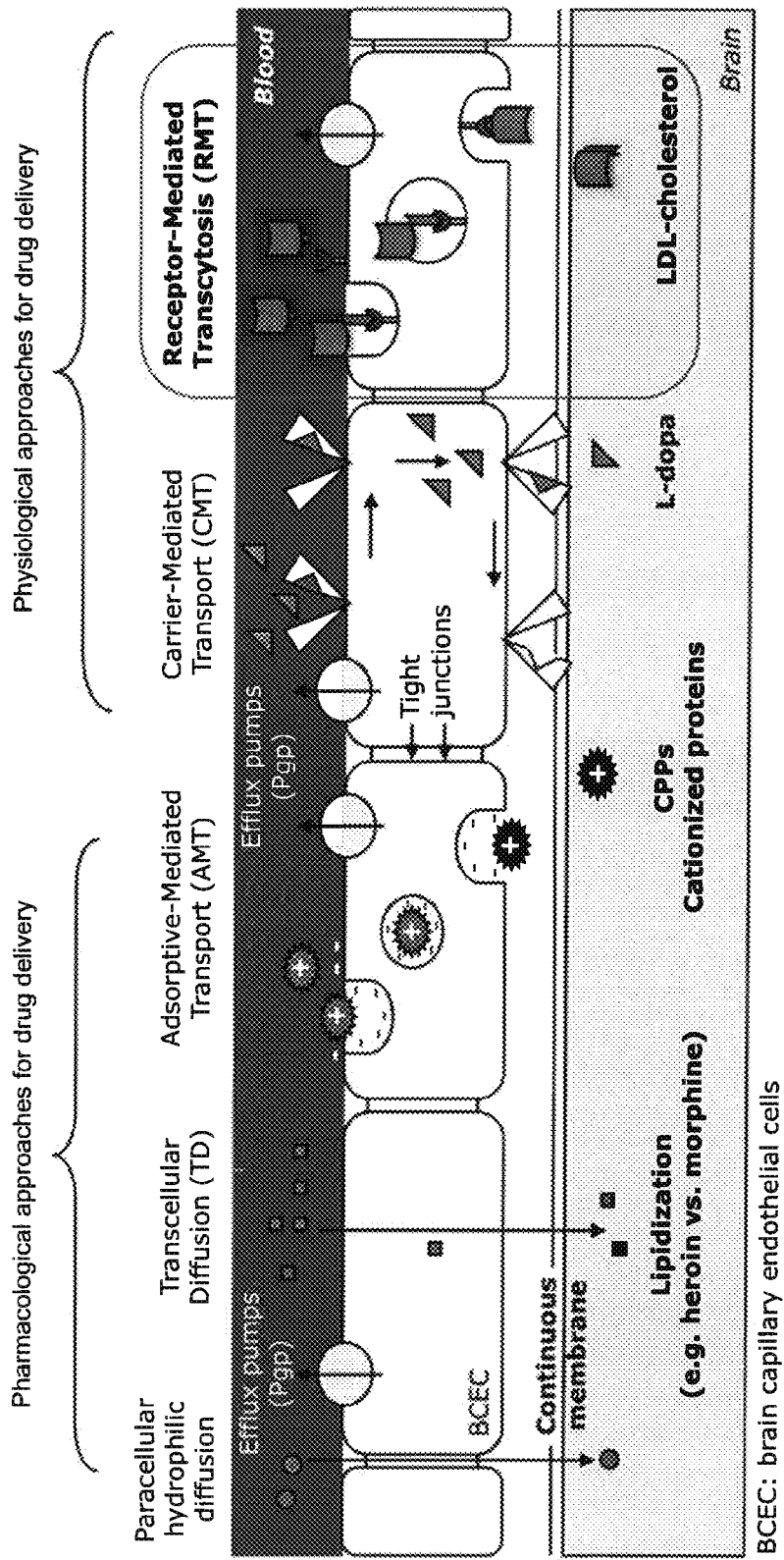
FIG. 1. Diagram illustrating the various modes of passage of natural or pharmacological molecules across the BBB, adapted from Abbott and Romero, 1996, *Mol. Med. Today*, 2(3), 106-113.
Figure 2:
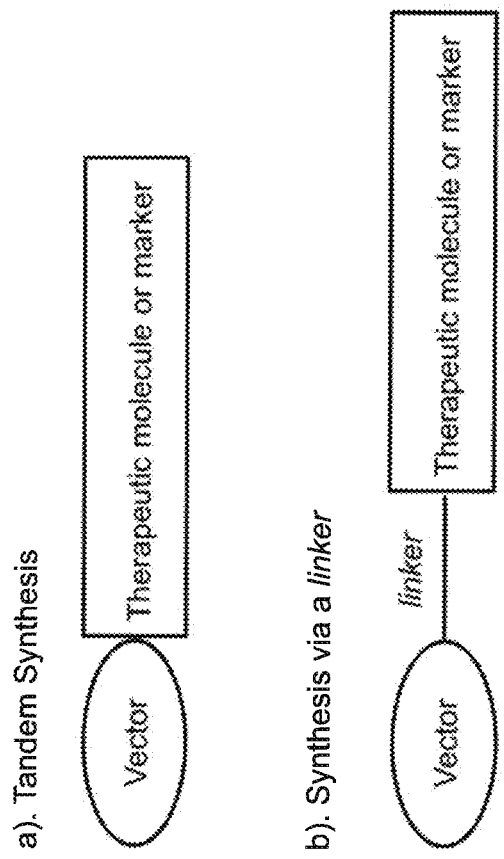
FIG. 2. Comparative diagram of synthesis in tandem and synthesis via a linker of a vector/molecule of therapeutic interest conjugate.

It is preferable that the interaction is sufficiently strong so that the peptide is not dissociated from the active substance before having reached its site of action. For this reason, the preferred coupling of the invention is covalent coupling, but non-covalent coupling could also be used. The substance of interest can be coupled directly with the peptide (synthesis in tandem) either at one of these terminal ends (N-term or C-term), or at a side chain of one of the constitutive amino acids of the sequence. The substance of interest can also be coupled indirectly by means of a linker or spacer, either at one of the terminal ends of the peptides, or at a side chain of one of the constitutive amino acids of the sequence (FIG. 2). Means of covalent chemical coupling, calling upon a spacer or not, include those selected from bi- or multifunctional agents containing alkyl, aryl or peptide groups by esters, aldehydes or alkyl or aryl acids, anhydride, sulfhydryl or carboxyl groups, groups derived from cyanogen bromide or chloride, carbonyldiimidazole, succinimide esters or sulfonic halides.

In this respect, the invention also relates to a method for preparing a conjugate compound such as defined above, characterized in that it comprises a step of coupling between a peptide or pseudo-peptide V and a substance D, if need be via L, preferably by a chemical, biochemical or enzymatic pathway, or by genetic engineering.

The invention also relates to a pharmaceutical composition characterized in that it comprises at least one conjugate compound such as defined above and one or more pharmaceutically acceptable excipients.

The invention also relates to a diagnostic composition characterized in that it comprises a diagnostic or medical imaging agent composed of a conjugate compound such as defined above.

The conjugate can be used in the form of any pharmaceutically acceptable salt. The expression "pharmaceutically acceptable salts" refers to, for example and in a non-restrictive way, pharmaceutically acceptable base or acid addition salts, hydrates, esters, solvates, precursors, metabolites or stereoisomers, said vectors or conjugates loaded with at least one substance of interest.

The expression "pharmaceutically acceptable salts" refers to nontoxic salts, which can be generally prepared by reacting a free base with a suitable organic or inorganic acid. These salts preserve the biological effectiveness and the properties of free bases. Representative examples of such salts include water-soluble and water-insoluble salts such as acetates, N-methylglucamine ammonium, amsonates (4,4-diaminostilbene-2,2'-disulphonates), benzenesulphonates, benzoates, bicarbonates, bisulphates, bitartrates, borates, hydrobromides, bromides, buryrates, camsylates, carbonates, hydrochlorates, chlorides, citrates, clavulanates, dichlorhydrates, diphosphates, edetates, calcium edetates, edisylates, estolates, esylates, fumarates, gluceptates, gluconates, glutamates, glycolylarsanylates, hexafluorophosphates, hexylresorcinates, hydrabamines, hydroxynaphthoates, iodides, isothionates, lactates, lactobionates, laurates, malates, maleates, mandelates, mesylates, methylbromides, methylnitrates, methylsulphates, mucates, napsylates, nitrates, 3-hydroxy-2-naphthoates, oleates, oxalates, palmitates, pamoates (1,1-methylene-bis-2-hydroxy-3-naphtoates, or emboates), pantothenates, phosphates, picrates, polygalacturonates, propionates, p-toluenesulphonates, salicylates, stearates, subacetates, succinates, sulphates, sulphosalicylates, suramates, tannates, tartrates, teoclates, tosylates, triethiodides, trifluoroacetates and valerianates.

The compositions of the invention advantageously comprise a pharmaceutically acceptable vector or excipient. The pharmaceutically acceptable vector can be selected from the vectors classically used according to each mode of administration. According to the mode of administration envisaged, the compounds can be in solid, semi-solid or liquid form. For solid compositions such as tablets, pills, powders, or granules that are free or are included in gelatin capsules, the active substance can be combined with: a) diluents, for example lactose, dextrose, sucrose, mannitol, sorbitol, cellulose and/or glycine; b) lubricants, for example silica, talc, stearic acid, its magnesium or calcium salt and/or polyethylene glycol; c) binders, for example magnesium and aluminum silicate, starch paste, gelatin, tragacanth, methylcellulose, sodium carboxymethyl cellulose and/or polyvinylpyrrolidone; d) disintegrants, for example starch, agar, alginic acid or its sodium salt, or effervescent mixtures; and/or d) absorbents, dyes, flavoring agents and sweeteners. The excipients can be, for example, mannitol, lactose, starch, magnesium stearate, sodium saccharin, talc, cellulose, glucose, sucrose, magnesium carbonate and analogues of pharmaceutical quality. For semi-solid compositions such as suppositories, the excipient can, for example, be an emulsion or oily suspension, or polyalkylene glycol-based, such as polypropylene glycol. Liquid compositions, in particular injectables or those included in a soft capsule, can be prepared, for example, by dissolution, dispersion, etc., of the active substance in a pharmaceutically pure solvent such as, for example, water, physiological saline solution, aqueous dextrose, glycerol, ethanol, oil and analogues thereof.

The compositions or conjugates of the invention can be administered by any suitable route and, in a non-restrictive way, by parenteral route, such as, for example, in the form of preparations that can be injected by subcutaneous, intravenous or intramuscular route; by oral route (or per os), such as, for example, in the form of coated or uncoated tablets, gelatin capsules, powders, pellets, suspensions or oral solutions (one such form for oral administration can be either with immediate release or with extended or delayed release); by rectal route such as, for example, in the form of suppositories; by topical route, in particular by transdermal route, such as, for example, in the form of patches, pomades or gels; by intranasal route such as, for example, in aerosol and spray form; by perlingual route; or by intraocular route.

The pharmaceutical compositions typically comprise an effective dose of a peptide or pseudo-peptide or conjugate of the invention. A "therapeutically effective dose" as described herein refers to the dose that gives a therapeutic effect for a given condition and administration schedule. It is typically the average dose of an active substance to administer to appreciably improve some of the symptoms associated with a disease or a pathological state. For example, in treating a cancer of the brain or of another tissue, a pathology, a lesion or a disorder of the CNS, the dose of an active substance that decreases, prevents, delays, eliminates or stops one of the causes or symptoms of the disease or disorder would be therapeutically effective.

A "therapeutically effective dose" of an active substance does not necessarily cure a disease or disorder but will provide a treatment for this disease or disorder so that its appearance is delayed, impeded or prevented, or its symptoms are attenuated, or its term is modified or, for example, is less severe, or the recovery of the patient is accelerated.

It is understood that the "therapeutically effective dose" for a person in particular will depend on various factors, including the activity/effectiveness of the active substance, its time of administration, its route of administration, its rate of elimination and its metabolism, drug combinations/interactions and the severity of the disease (or disorder) treated on a preventive or curative basis, as well as the age, weight, overall health, sex and/or diet of the patient.

Depending on the substance coupled, the conjugates and compositions of the invention can be used for treating, preventing, diagnosing or imaging numerous pathologies, notably pathologies affecting the CNS or the eye, infectious pathologies or cancers, inflammatory disease, and/or hepatic cirrhosis or fibrosis.

In this respect, the invention relates to the use of pharmaceutical conjugates or compositions as described above for treating or preventing CNS pathologies or disorders, brain tumors or other cancer cells, and bacterial, viral, parasitic or fungal infectious pathologies of the brain or other tissues, inflammatory disease, and/or hepatic cirrhosis or fibrosis.

The invention also relates to the use of the pharmaceutical conjugates or compositions as described above for diagnosing or imaging CNS or ocular pathologies or disorders, brain tumors or other cancer cells, and bacterial, viral, parasitic or fungal infectious pathologies of the brain or other tissues and inflammatory disease, and/or hepatic cirrhosis or fibrosis.

The invention also relates to the use of a conjugate or composition such as defined above for treating, imaging and/or diagnosing a brain tumor or other types of cancer cells. Studies have indeed shown that patients with certain cancers have hypocholesterolemia. This hypocholesterolemia is the consequence of an overuse of cholesterol by cancer cells. The latter to survive induce an increase in the level of LDLR expression within organs with tumors (Henricksson et al., 1989, Lancet, 2(8673), 1178-1180). There is thus a correlation between the increase in the level of LDLR expression by cells and certain cancers. It has also been recently shown that the number of LDLR is very high on the surface of certain pathological cells such as cancer cells. It is generally accepted that 1000 to 3000 LDLR are present at the surface of a non-pathological cell. Similarly, few LDLR are present in the cells of the gray matter of the cortex (Pitas et al., 1987, J. Biol. Chem., 262, 14352-14360). In the case of the glioblastoma, LDLR overexpression has been shown. Thus, on the surface of brain tumor cells, 125,000 (for U-251 cells) to 900,000 (for SF-767 cells) LDLR have been counted (Malentiska et al., 2000, Cancer Res., 60, 2300-2303; Nikanjam et al., 2007, Int. J. Pharm., 328, 86-94). It should also be noted that many tumor cells overexpress LDLR, such as those of prostate cancer (Chen et al., 2001, Int. J. Cancer, 91, 41-45), colon cancer (Niendorf et al., 1995, Int. J. Cancer, 61, 461-464), leukemia (Tatidis et al., 2002, Biochem. Pharmacol., 63, 2169-2180), colorectal cancer (Caruso et al., 2001, Anticancer Res., 21, 429-433), breast cancer (Graziani et al., 2002, Gynecol. Oncol., 85, 493-497), as well as cancers of the liver, pancreas, ovaries, lung, etc.

The invention also relates to the use of a conjugate or composition such as defined above for treating, imaging and/or diagnosing bacterial, viral, parasitic or fungal infectious pathologies of the brain or other tissues, such as, and in a non-restrictive way, AIDS or meningitis, etc. LDLR is also present on hepatic cells. It is now known that endocytosis of the hepatitis C virus (HCV) can occur via LDLR. LDLR could serve as a viral receptor at an early stage of infection of human hepatocytes by HCV (Molina et al., 2007, J. Hepatol., 46(3), 411-419). The inventive conjugates can thus be used to specifically target pathological cells, infected by viruses such as those of hepatitis B and hepatitis C that express LDLR and/or to modulate via LDLR the viral infection process of healthy cells. The invention also relates to the use of a conjugates or composition such as defined above for treating, imaging and/or diagnosing other hepatic pathologies such as, and in a non restrictive way, non viral hepatitis provoked or not by alcohol consumption, acute hepatic inflammation, hepatic cirrhosis or fibrosis, primary biliary cirrhosis and other pathologies of the hepatobiliary tract, etc (Poeltra et al., 2012, J Control Release, 161(2):188-97).

The invention also relates to the use of a conjugate or composition such as defined above for treating, imaging and/or diagnosing neurodegenerative pathologies such as, in a non-restrictive manner, Alzheimer's disease, Parkinson's disease, Creutzfeldt-Jakob disease, cerebrovascular accidents (CVA), bovine spongiform encephalopathy, multiple sclerosis, amyotrophic lateral sclerosis, spinal cord injuries etc.

The invention also relates to the use of a conjugate or composition such as defined above for treating, imaging and/or diagnosing neurological pathologies such as, in a non-restrictive manner, epilepsy, migraine, encephalitis, CNS pain, etc.

The invention also relates to the use of a conjugate or composition such as defined above for treating, imaging and/or diagnosing neuropsychiatric pathologies such as, in a non-restrictive manner, depression, autism, anxiety, schizophrenia, etc.

The invention also relates to the use of a conjugate or composition such as defined above for treating, imaging and/or diagnosing pathologies of the eye such as, in a non-restrictive manner, retinitis pigmentosa, macular degeneration, cone-rod dystrophy (CORD), retinal separation, retinal detachment, hypertensive retinopathy and diabetic retinopathy, retinoblastoma, lipemia retinalis, etc.

The terms "treatment," "treating," "treat" and other similar expressions refer to obtaining a pharmacological and/or physiological effect, for example, inhibition of cancer cell growth, cancer cell death or improvement of a disease or neurological or ocular disorder. The effect can be prophylactic or preventive in order to completely or partially prevent the aggravation of a disease or a symptom such a disease, in an ill person, or its propagation, in healthy subjects, and/or can be therapeutic in order to completely or partially treat a disease and/or its related harmful effects. The term "treatment" as used in the present document covers any treatment of a disease in a mammal, and more particularly in man, and comprises: (a) prevention of a disease (for example, prevention of cancer) or a condition that can arise in a person predisposed to this pathology or disorder, but who has not yet been positively diagnosed, (b) the slowing of a disease (for example, by stopping its development), or (c) relief from a disease (for example, by reducing the symptoms associated with a disease). This term "treatment" also covers any administration of an active substance in order to tend, cure, relieve, improve, decrease or inhibit a condition in an individual or patient, including, but not limited to, the administration to a person in need of a drug composed of a vector or conjugate as described in the present document.

The present invention also relates to the use of a peptide or pseudo-peptide of the invention to increase the biological activity of an active substance or of a substance of interest (therapeutic molecule of interest, diagnostic or medical imaging agent, or any other molecule such as a molecular probe) to which it is coupled.

The present invention also relates to the use of a peptide or pseudo-peptide of the invention to decrease the toxicity of an active substance or of a substance of interest (therapeutic molecule of interest, diagnostic or medical imaging agent, or any other molecule such as a molecular probe) to which it is coupled.

Other aspects and advantages of the present invention will become apparent upon consideration of the examples below, which are only illustrative in nature and which do not limit the scope of the present application.

EXAMPLES

Example I

Construction of Cho Cell Lines Stably Expressing Human Mouse and Rat LDLR

The inventors identified peptides on the basis of their interaction with and affinity for human mouse and rat low-density lipoproteins receptors (hLDLR, mLDLR and rLDLR respectively), which are notably involved in the endocytosis and transcytosis (transcellular transport) of cholesterol. The prerequisite to the characterization of these peptides was the establishment in eukaryotic cells (Chinese hamster ovary cells, CHO) of stable cell lines expressing hLDLR, mLDLR and rLDLR constitutively and at high rates. These cell lines are used: i) for the characterization of peptides binding to hLDLR expressed at the cell surface, in its native configuration; ii) to verify that hLDLR, mLDLR and rLDLR can internalize the selected peptides by endocytosis.

The construction of these cell lines (except the cell line expressing rLDLR) has been described in application WO2010/046588. Briefly, the messenger RNA sequences coding for hLDLR, mLDLR and rLDLR are available in databases (accession numbers: NM_000527, NM_010700 and NM_175762.2, respectively). The primers necessary for cDNA amplification by PCR were selected, comprising at their end (in bold type) the restriction sites necessary (HindIII and SalI for human LDLR and HindIII and KpnI for mouse and rat LDLR) for cloning in the pEGFP-N1 expression vector (Clontech):

```
hLDLR
Forward primer:
                                    (SEQ ID NO: 18)
ATATATAAGCTTCGAGGACACAGCAGGTCGTGAT Reverse primer:
                                    (SEQ ID NO: 19)
TTAATTGTCGACCACGCCACGTCATCCTCCAGACT mLDLR
Forward primer:
                                    (SEQ ID NO: 20)
ATATATAAGCTTGACGCAACGCAGAAGCTAAG Reverse primer:
                                    (SEQ ID NO: 21)
TTAATTGGTACCGTTGCCACATCGTCCTCCAG rLDLR
Forward primer:
                                    (SEQ ID NO: 22)
ATATATAAGCTTACATTTCGGGTCTGTGATCC Reverse primer:
                                    (SEQ ID NO: 23)
TTAATTGGTACCCATGCCACATCATCCTCCAG
```

Figure 3A:
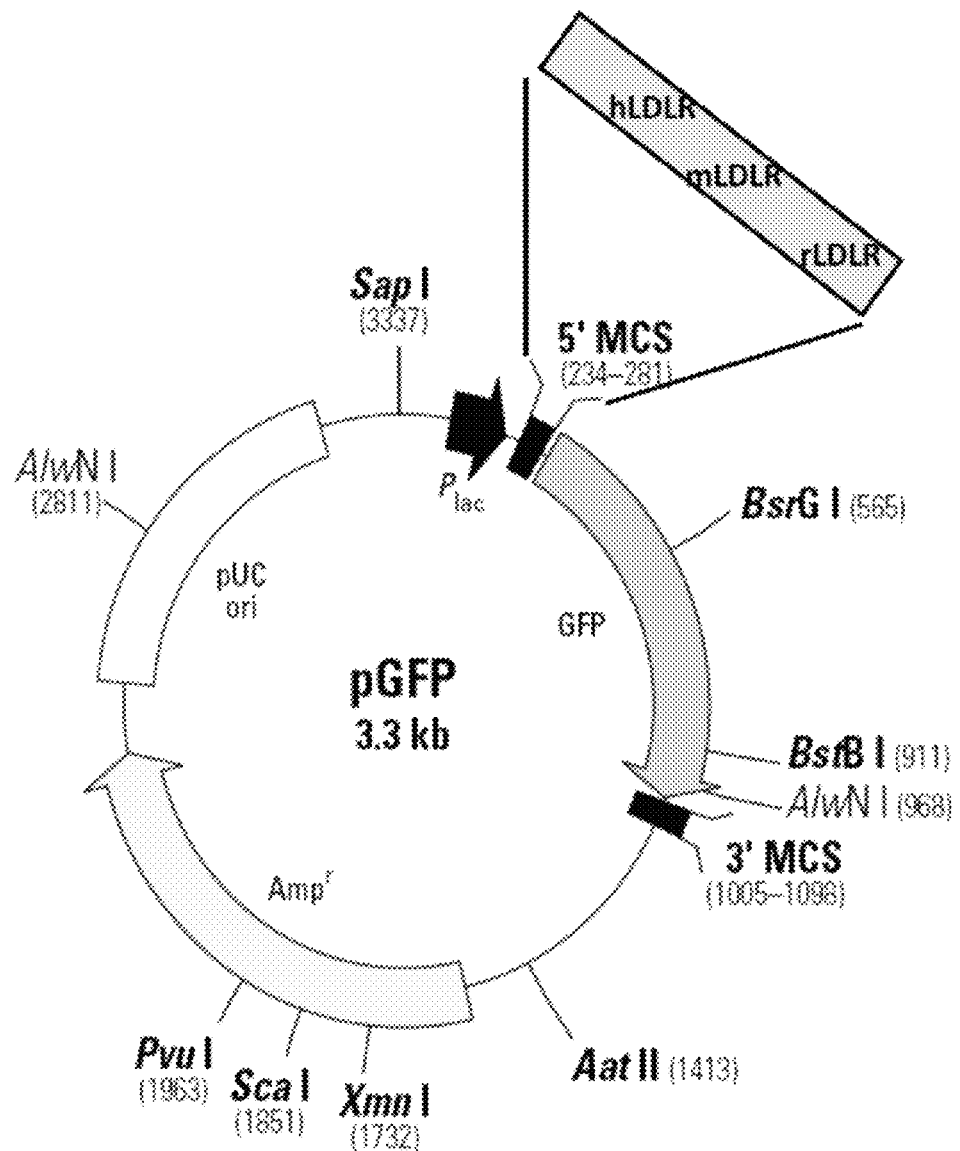
FIG. 3. A—Diagram of the plasmid used for cloning hLDLR mLDLR and rLDLR. B—Diagram representing the fusion protein expressed by transfected cells.
Figure 3B:
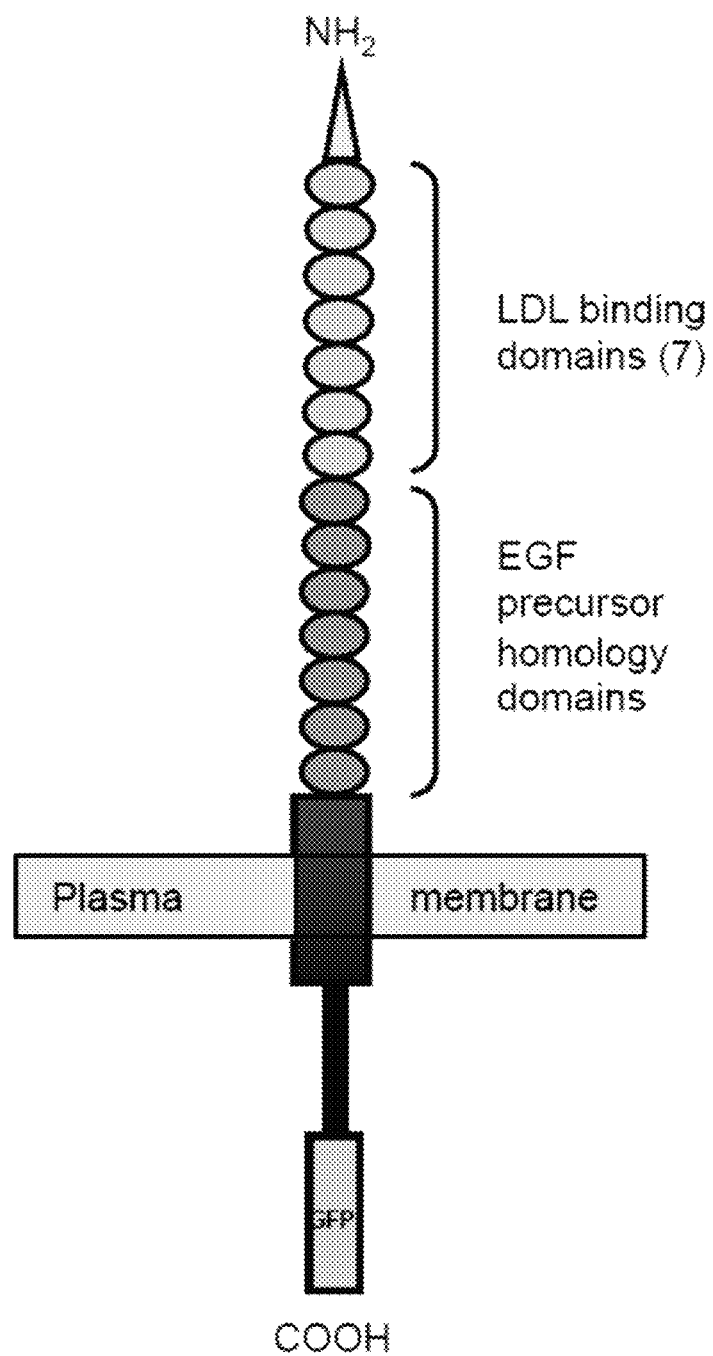

Total RNA prepared from human mouse and rat brains were transformed into cDNA by reverse transcription for PCR amplification of DNA fragments coding for hLDLR and mLDLR. After amplification, the PCR products were digested by HindIII-SalI or HindIII-KpnI restriction enzymes, and ligated in the pEGFP-N1 expression vector (Clontech), digested by the same restriction enzymes. After transfection in eukaryotic cells, this vector enables the expression, under control of the CMV promoter, of LDLR fused with GFP at their C-term end, i.e., at the end of their intracellular domains (FIG. 3). After transforming competent E. coli DH5a bacteria, obtaining isolated colonies and preparing plasmid DNA, both strands of the constructions were sequenced in their entirety for verification.

Figure 4:
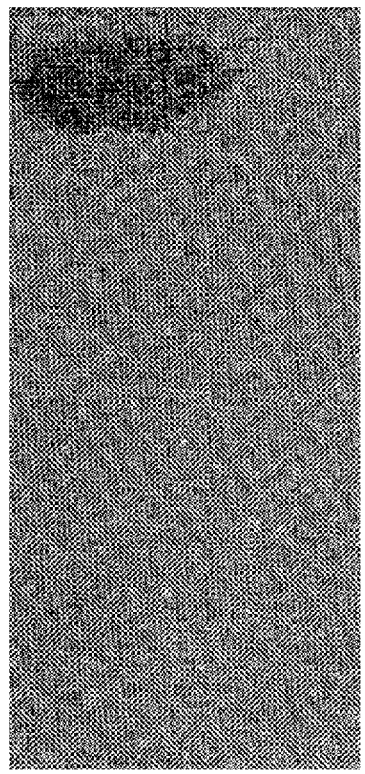
FIG. 4. Western blot performed on CHO cell lines expressing constitutively hLDLR-GFP or GFP (control) fusion proteins. A 190 kDa band corresponding to the size of the hLDLR-GFP fusion protein is detected with anti-hLDLR antibody.

Transient transfections in various cell lines (CHO, COS, N2A and HEK293) were carried out to determine on living or fixed cells the expression levels and membrane location of hLDLR and mLDLR. The receptor is directly visible on living cells, under fluorescence microscopy, without the need for immunostaining, by virtue of green fluorescence emitted by GFP fused at the C-term of these receptors. Stable transfectants were selected by limit dilution and by the geneticin resistance gene (G418) carried by the expression vector. These cell lines were amplified while maintaining selective pressure. In the example cited here, the expression of hLDLR-GFP of the expected size was verified by Western blot on cell lysates with antibodies directed against human LDLR and against GFP. A protein corresponding to the combined sizes of GFP and hLDLR (190 kDa) is recognized by anti-hLDLR (FIG. 4) and anti-GFP antibodies in cell extracts prepared from stable cell lines. A CHO cell line expressing GFP constitutively was used as negative control. The anti-hLDLR antibody detects no protein in the GFP cell line.

Figure 5:
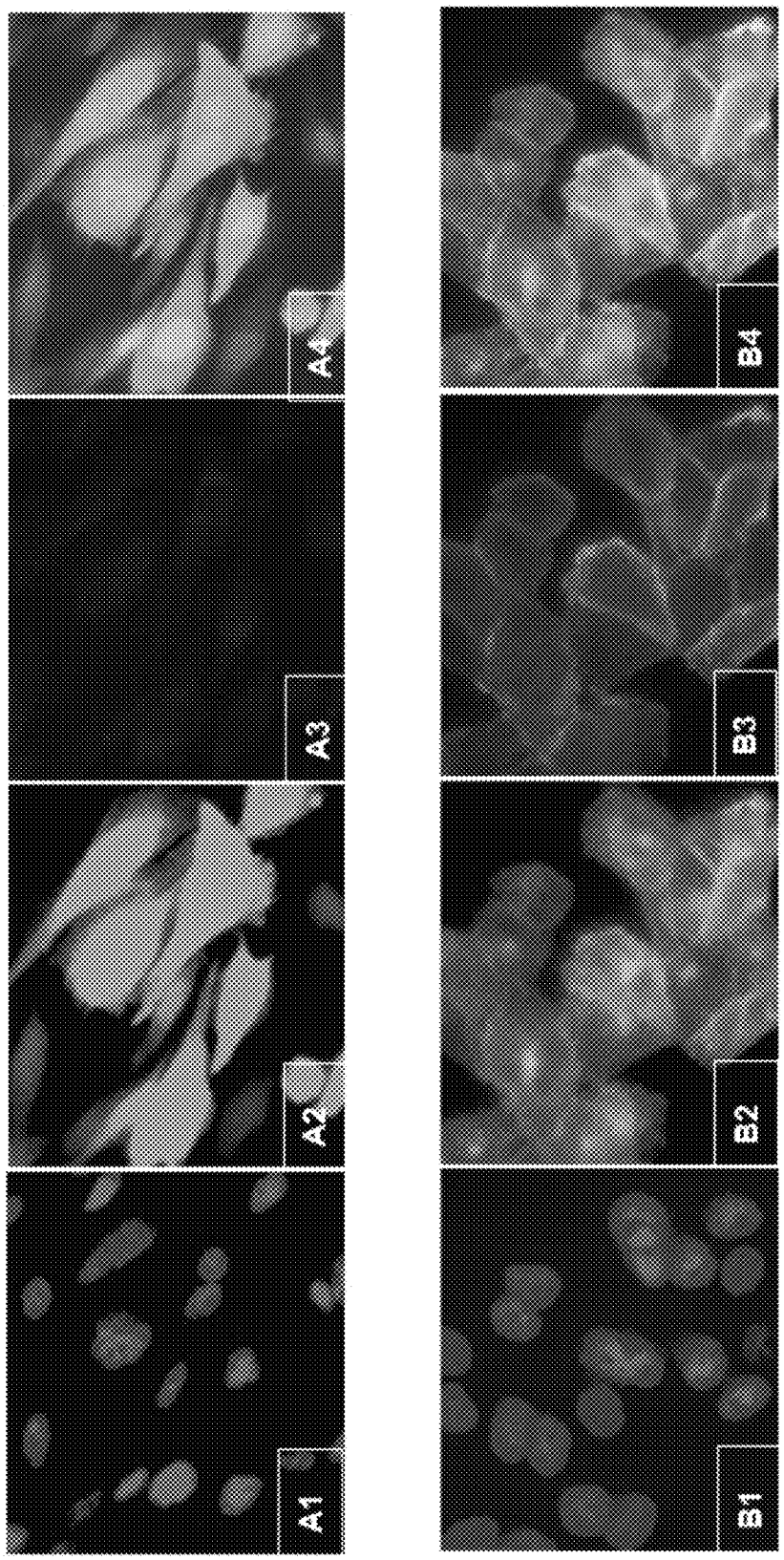
FIG. 5. Immunocytochemistry on non-permeabilized CHO cells, stably expressing either A—GFP alone (control), or B—the hLDLR-GFP fusion protein. Cell nuclei are stained with Hoechst (blue, A1 and B1). GFP fluorescence is visible in green (A2 and B2), that of the staining of the extracellular domain of hLDLR by anti-hLDLR antibody is visible in red (A3 and B3) and the superimposing of red and green stains is visible in yellow/orange (A4 and B4). Note that only the cells stably transfected with the hLDLR-GFP fusion protein express the membrane receptor (B3).

Immunocytochemistry with anti-hLDLR antibody on fixed (PFA) cells of the CHO-GFP (control) and CHO-hLDLR-GFP cell lines shows that hLDLR-GFP fusion is well expressed in the transfected cells. Immunocytochemistry experiments on non-permeabilized cells with Triton X100 show that the extracellular domain of LDLR is well detected at the extracellular level (FIG. 5).

Figure 6:
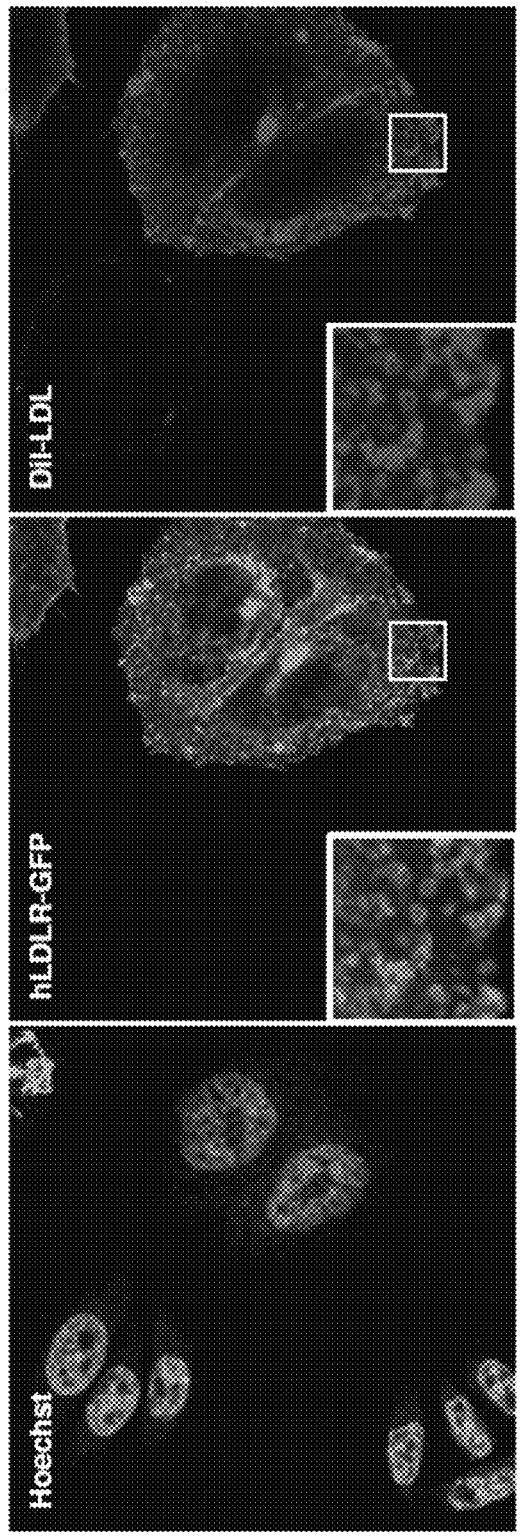
FIG. 6. CHO-hLDLR-GFP cells grown on coverslips are incubated with DiI-LDL for 15 minutes. Cells are fixed and nuclei are stained using Hoechst. Insets show higher magnification of a representative area of confocal images and indicate a strong colocalization between hLDLR-GFP-containing endosomes and LDLs, confirming that the CHO-hLDLR-GFP cell line expresses a functional LDLR that undergoes endocytosis upon binding of its natural ligand.

Colocalization between hLDLR and its natural ligand LDL, made fluorescent by adsorption of DiI, a fluorescent marker, is shown. This natural fluorescent ligand (DiI-LDL) is rapidly internalized (endocytosis) as visualized under fluorescence microscopy on fixed cells (FIG. 6-A). In contrast, DiI-LDL is not incorporated by endocytosis by the control CHO-GFP cell line, or by another control CHO cell line, which overexpresses, for example, human hTfR (FIG. 6-B), another receptor involved in transcytosis. Moreover, endocytosis activity of the CHO-LDLR-GFP cell line is specific to LDLR ligand since in this cell line endocytosis of ligand not specific for it, for example Tf stained with red fluorochrome (Texas Red, FIG. 6-C), is not observed.

Receptor functionality (endocytosis capacity) is confirmed by real-time experiments, under video fluorescence microscopy showing that DiI-LDL is actually transported rapidly and very efficiently in cells expressing hLDLR-GFP compared with cells expressing GFP alone or cells expressing another receptor involved in endocytosis such as hTfR (negative control). Conversely, video microscopy experiments carried out with Tf stained with Texas Red, which is very efficiently incorporated by endocytosis in cells expressing hTfR-GFP, confirm that Tf is not incorporated by endocytosis by cells of a control GFP cell line or by cells of an hLDLR cell line.

In spite of a high hLDLR expression level in CHO-hLDLR-GFP cell lines, the endocytosis system is not only effective, but it preserved its selectivity. The presence of GFP fusion altered neither the membrane insertion properties of hLDLR, exposure outside the cell of the hLDLR extracellular domain, nor the functionality of the receptor in endocytosis processes.

Example II

Synthesis of peptides and coupling with a tracer molecule (biotin, fluoresceins, rhodamines, cyanines or STag with enzymatic activity).

Peptides were synthesized by the solid phase peptide synthesis (SPPS) method on an Advanced ChemTech Apex396 (AAPPTec) synthesizer, or a LIBERTY™ (CEM) microwave synthesizer, using an Fmoc/tBu strategy on Rink Amide AM resin on polystyrene-1% DVB, Wang on polystyrene-1% DVB, Barbs (2-chlorotrityl chloride) on polystyrene-1% DVB, or Sieber Amide on polystyrene-1% DVB. The load (or substitution) is between 0.25 mmol/g and 1.6 mmol/g according to the resin used.

The amino acids N-protected by Fmoc (or Boc for certain N-term ends) and/or protected by orthogonal functions (notably acid labile functions) at their side chains, the chemical coupling and deprotection reagents and the solvents are bought from specialized companies and are used as-is.

The Rink Amide and Wang resins make it possible to synthesize peptide sequences completely deprotected on their side chains and their C-term ends. This is thus 2-dimension (Fmoc/tBu) orthogonal SPPS.

Barlos and Sieber hypersensitive acid labile (HAL) resins respectively enable the release of the terminal (C-term) acid or amide function while preserving the orthogonal side protections of the various amino acids of the synthesized peptide as well as the terminal (N-term) amine protection of the amine function of its last amino acid (for example, N-acetylation for questions of stability of the neosynthesized peptide sequence). These type of resins, via an Fmoc ($Prot_1$) synthesis strategy, makes it possible to use acid-labile orthogonal side protections ($Prot_2$: Boc, tBu, OtBu, Trt, Mmt, Acm, etc.) cleavable only in strongly acid medium, whereas the protected peptide is cleaved in very weak acid conditions. This type of cleavage makes it possible to recover the peptide sequence completely protected on its side functions ($Prot_2$) with a view in particular to coupling a therapeutic molecule of interest with the peptide. This is thus three-dimension (Barlos or Sieber/Fmoc/tBu) orthogonal SPPS.

The standard orthogonal side protections ($Prot_2$) used for each amino acid during peptide synthesis are: Arg(N-Pbf), Arg(N-Pmc), Asn(N-Trt), Asp(O-tBu), Cys(S-Acm), Cys(S-Mmt), Cys(S-4MeBn), Cys(S-tBu), Cys(S-Tmob), Cys(S-Trt), Glu(O-tBu), Gln(N-Trt), His(N-Trt), Lys(N-Boc), Pen(S-Acm), Pen(S-Trt), Ser(O-tBu), Thr(O-tBu), Trp(N-Boc), Tyr(O-tBu) (Applied Biosystems, 1998, Cleavage, Deprotection, and Isolation of Peptides after Fmoc Synthesis. Technical Bulletin). Gly, Sar, Ala, Val, Leu, Ile, Phe, Met, Pro, Pip and Thz do not have side protections, since their respective chemical structures do not require it.

Amino acids are coupled via activation of the acid function of the n+1 amino acid using DIEA/HBTU/HOBt or DIPC/HOBt in DMF.

Deprotection of the Fmoc ($Prot_1$) group of a new amino acid thus coupled is carried out using 20% piperidin in DMF.

The last amino acid coupled during peptide sequencing will either be protected by a Boc function (with a view to releasing its free terminal amine function at the end of synthesis), or acetylated (in order to stabilize the synthesized neopeptide but also to reduce the risks of secondary reactions during covalent coupling of the therapeutic molecule of interest in the C-term position, for example) or propionylated.

According to the peptide synthesized, disulfide bridges are obtained by intramolecular cyclisation from two thiol functions of two suitably protected Cys (Acm, Trt, tBu, etc.), either in solution or on resin, using reagents classically used by those persons skilled in the art: $H_2O/AcOH/ANH_4)_2CO_3/DMSO$, $H_2O/AcOHANH_4)_2CO_3$, $I_2/DMF$, $I_2/HFIP/DCM$, $TFA/DMSO/anisole$, $I_2/DCM/MeOH/H_2O$, etc. A Cys in the N-term position can advantageously be replaced by Pen or Mpa for cyclisation via a disulfide bridge. Lanthionine bridges (by cyclisation via dehydroalanine) or dicarba (by cyclisation via allylGly) can also be obtained by synthesis pathways known to those persons skilled in the art. A lactam bridge can be created between the side acid function of a Glu (or Asp) residue and a side amine function on a Lys or an N-term amine. Similarly, cyclisation between the N-term amine function and the C-term acid function (head/tail) can be carried out via an amide bond, just as cyclisation between the side amine function of Lys and the C-term acid function of the peptide.

Peptides from Barlos or Sieber resins are cleaved by methods classically used by those persons skilled in the art, either with 0.5% TFA (v/v) in DCM, or with AcOH/TFE/DCM (1/1/3), or with HFIP (30%) in DCM, or with TFE (30%) in DCM, etc Deprotection of side chains, and cleavage of peptides from Rink Amide or Wang resins, are carried out by methods classically used by those persons skilled in the art: either with $TFA/H_2O/TIS$ or TIPS (95/2.5/2.5), or with $TFA/H_2O/EDT/TIS$ or TIPS (94/2.5/2.5/1), or with TFA/thioanisole/$H_2O$ (94/5/1), or with TFA/TIS/$H_2O$/thioanisole (90/5/3/2), or with TFA/$H_2O$/phenol/thioanisole/EDT (82.5/5/5/5/2.5), etc.

Biotins, fluoresceins, (FITC), rhodamines (rhodamine RED-X), cyanines (Cy3.5) or STag (see EXAMPLE IV, below) are generally introduced in the C-term or N-term position, these tracers are sometimes couples coupled in the N-term position, according to classic synthesis and coupling methods known to those persons skilled in the art.

Peptides are isolated and purified by HPLC on a Beckman System Gold 126 apparatus with a Chromolith C18 (4.6 mm×50 mm) or Nucleosil C18 (10 mm×250 mm) column with, for example, a 0% to 100% acetonitrile gradient in an aqueous phase ($H_2O$+0.1% TFA) in 3.5 min then 100% to 0% in 1.5 min (flow rate: 1 ml/min to 5 ml/min), or on a Waters 1525 system with a Chromolith Speed ROD RP-18 (4.6 mm×50 mm) column (stationary phase) with detection by a Waters 996 PDA detector (190 nm-400 nm), or on a Waters Alliance 2690 system with a Chromolith Performance RP-18 (3 mm×100 mm) column (stationary phase) with detection by a Waters 996 PDA detector (190 nm-400 nm). UV detection is carried out at 214 nm and 254 nm.

Preparative purifications are carried out with a Waters Prep LC 4000 system with a GUARD-PAK™ column (stationary phase) with DELTA-PAK™ C18 cartridges (25 mm×10 mm) with detection by a Waters 2487 Dual Wavelength Absorbance Detector.

Molecular weights are determined using an electrospray ionization (ESI) mass spectrometer in positive mode. The spectra are obtained by using a Waters Micromass Quattro Micro (quadrupole analyzer) equipped with a Waters Alliance 2690 HPLC system enabling LC-MS coupling.

The LC-MS analysis conditions used are as follows:
Chromolith Flash C18 column (4.6 mm×25 mm),
3 ml/min flow rate,
linear gradient from 0% to 100% of B in 2.5 min (A: 0.1% $H_2O/HCO_2H$; B: 0.1% $ACN/HCO_2H$).

Mass spectra in positive electrospray mode are acquired at a flow rate of 100-200 μl/min. The data are obtained in scan mode from 200-1700 m/z with 0.1 s intervals.

Example III

Peptide Vectors Design

The peptide of sequence SEQ ID NO: 17/STag, described in application WO2010/046588, was used as the reference.

From this peptide, various approaches were used to try to improve binding, synthesis and vectorization properties. Many peptides were thus synthesized, differing from SEQ ID NO: 17 by the deletion and/or the replacement and/or the chemical modification of one or more amino acid residues.

The capacity of the peptides thus synthesized to bind hLDLR was determined.

To this end, adherent and confluent CHO-hLDLR-RFP cells were cultivated in 6-well plates. Three wells of cells are used per condition.

A solution containing 10 μM of peptide SEQ ID NO: 17/STag was prepared in HamF12-1% BSA culture medium. To this solution was added 10 μM of the peptide to evaluate (competition).

Several control solutions are also prepared:
(i) HamF12-1% BSA medium.
(ii) HamF12-1% BSA medium+10 μM control peptide CTRL-STag (evaluation of nonspecific binding of any peptide comprising an STag).
(iii) HamF12-1% BSA medium+10 μM peptide SEQ ID NO: 17/STag+10 μM control peptide CTRL (evaluation of "nonspecific" competition between the peptide of interest and the control peptide CTRL).

The FRET approaches used are those described in EXAMPLE IV.

The results obtained for the best peptides are presented in table 1 below. The table gives the results of the competitions in % of reference peptide vector (SEQ ID NO: 17/STag), affinity for hLDLR, displaced by the peptides of the invention. The larger the displacement value, the more affinity the peptide has for hLDLR. When this value is greater than 50%, the peptide has an affinity greater than that of the reference peptide (SEQ ID NO: 17).

TABLE 1

| Test peptides | Displacement of the control peptide |
| --- | --- |
| SEQ ID NO: 1 | 66% |
| SEQ ID NO: 2 | 70% |
| SEQ ID NO: 3 | 75% |
| SEQ ID NO: 4 | 88% |
| SEQ ID NO: 5 | 91% |
| SEQ ID NO: 6 | 77% |
| SEQ ID NO: 7 | 74% |
| SEQ ID NO: 8 | 84% |
| SEQ ID NO: 9 | 80% |
| SEQ ID NO: 10 | 54% |
| SEQ ID NO: 26 | 100% |
| SEQ ID NO: 27 | 93% |
| SEQ ID NO: 28 | 70% |
| SEQ ID NO: 29 | 67% |
| SEQ ID NO: 30 | 100% |
| SEQ ID NO: 11 | 22% |
| SEQ ID NO: 12 | 23% |
| SEQ ID NO: 13 | 8% |
| SEQ ID NO: 14 | 9% |
| SEQ ID NO: 15 | <5% |
| SEQ ID NO: 16 | <5% |
| SEQ ID NO: 17 | 50% |

The results presented show that some peptides, for example of sequences SEQ ID NOs: 1 to 10 and 26 to 30 have improved affinity for the human LDLR. These results are particularly interesting considering the small size of the peptides, and are particularly remarkable and surprising considering the negative effects on affinity observed with peptides SEQ ID NO: 11-16.

Based on the FRET results and to establish a hierarchy of peptides according to their specific binding to LDLR (Km), increasing concentrations of STag-conjugated peptide vectors are incubated in the presence or absence of the same peptide with no STag at concentrations sufficiently high to saturate the receptor population on the cells. It is shown that improvement of peptide vector binding to hLDLR in FRET experiments correlates with a decrease of Km values. For example, peptides SEQ ID NO: 17 (FRET displacement: 50%), SEQ ID NO: 4 (FRET displacement: 88%) and SEQ ID NO: 5 (FRET displacement: 91%), show Km values of 500, 97 and 143 nM, respectively. This range of Km seems appropriate for CNS drug delivery as it was shown that too high affinities of a vector entity (an antibody) for its target (the TfR) lead to poor drug delivery across the BBB, while reducing Km of the vector antibody for the TfR to the 100 nM range elicited drug release from the BBB into the brain (Yu et al., 2011, Sci Transl Med., May 25; 3(84):84ra44).

Thus, while being based on a medicinal chemistry optimization approach, the inventors progressed in the understanding of the structure/activity (affinity) relationships of the reference peptide vector (SEQ ID NO: 17), and in particular:
(i) the importance of each amino acid residue (Ala-scan, D-scan), i.e., the alternative replacement (one by one) of each original residue either by an alanine, or by their non-natural analogue of D configuration;
(ii) the importance of N- and C-term ends (acetylation, amidation, etc.);
(iii) the importance/advantage of cyclization of the peptide.

The principal limitations generally attributed to peptide derivatives used in therapeutics are:
(i) their low oral bioavailability (their administration by intravenous route is generally necessary);
(ii) a short half-life due to their rapid breakdown by proteolytic enzymes (in particular peptidases or proteases) of the digestive system and blood plasma;
(iii) their rapid elimination from circulating blood by the liver (hepatic clearance) and the kidneys (renal clearance);
(iv) their low capacity to pass through biological or physiological membranes because of their generally hydrophilic character;
(v) their great conformational flexibility, which may involve a lack of selectivity leading to interactions with different receptors or targets (resulting in weak specific biodistribution), which causes the activation of several targets and leads to side effects or undesirable effects;
(vi) the high costs of synthesis and industrial production (the production cost of a 5 kDa peptide are greater than the production cost of a 500 Da organic molecule).

In a rather remarkable way, the peptides or pseudo-peptides of the invention have the following pharmacological prerequisites:
(i) an affinity for hLDLR in the range of 100 nM for some of the peptides or pseudo-peptides which seems appropriate considering the objective of binding and endocytosis but also of intracellular- or post transcytosis/excretion-release of the peptide (Yu et al., 2011, Sci Transl Med., May 25; 3(84):84ra44);
(ii) physicochemical characteristics that favor their specificity for the hLDLR (constrained conformation via disulfide bridge cyclization; a size reduced to 8 amino acids; up to 4 non-natural amino acids for promoting their specificity for this receptor;
(iii) a greater resistance to enzymatic proteolysis because of their cyclization, the introduction of non-natural amino acids and for some a pseudo-peptide bond, but also by modifying/blocking the N- and C-term ends;

while endogenous peptides and generally small linear peptides containing only natural amino acids have very short in vitro half-lives ($t_{1/2}$) in blood, typically in the minute range (Foltz et al., 2010, *J Nutr.*, January; 140 (1):117-8), the $t_{1/2}$ of peptide SEQ ID NO: 17 for example is 3 hours.

(iv) a small size and a molecular weight near 1 Da making it possible to reduce the costs of synthesis and of future production on an industrial scale.

Example IV

Binding and endocytosis of synthesized peptides with affinity for hLDLR in CHO-LDLR-GFP cell lines.

Figure 7:
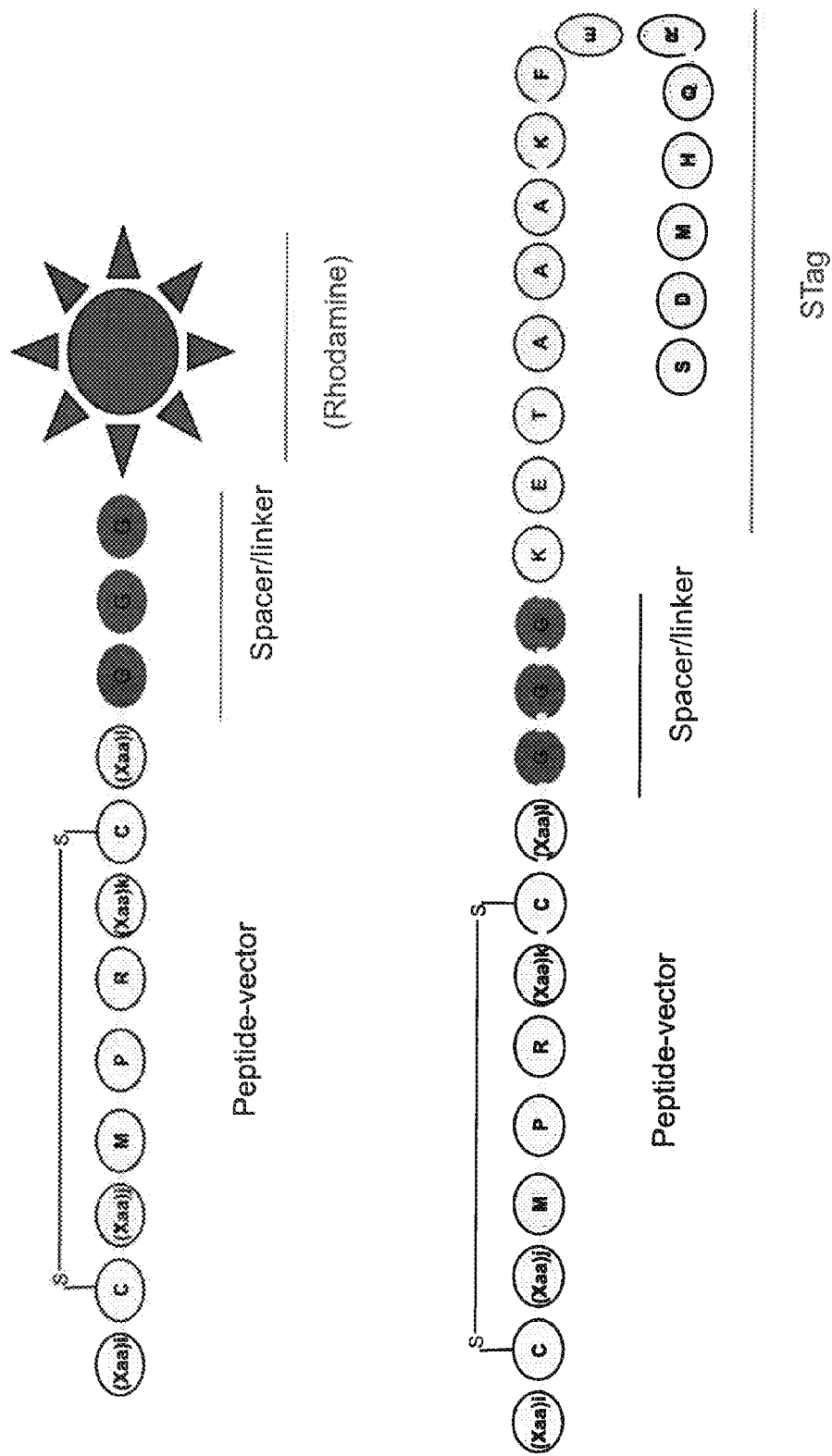
FIG. 7. General scheme of synthesized peptides conjugated with rhodamine or STag, with a C-terminus (C-term) spacer.

Peptides of the invention with affinity for hLDLR-GFP/ RFP are coupled/conjugated in the C-term or N-term position with various tracer molecules, either rhodamine Red-X, Cy3.5, FITC or STag, separated by a spacer generally composed of three Gly residues (FIG. 7). The STag (a 15 amino acid peptide derived from sequence 1-15 of bovine pancreatic ribonuclease A) on the one hand can be recognized by an anti-STag antibody for immunocytochemistry or FACS approaches, and on the other hand can reconstitute enzymatic activity by binding with ribonuclease S-protein (C-term portion, amino acids 21-124) in tests of activity in vitro using the FRETWorks STag assay kit (Novagen 70724-3). The ribonuclease thus activated digests an RNA substrate releasing a masked fluorescent agent visualized by FRET (fluorescence resonance energy transfer) and quantified in a 96-well plate in a Beckmann spectrofluorimeter. For these FRET experiments, control CHO cells were used and GFP fused in the C-term position with hLDLR and mLDLR, which generates strong background noise at the wavelengths used for FRET, was replaced by red fluorescent protein (RFP). The stable cell lines generated for the FRET experiments are thus CHO-RFP and CHO-hLDLR-RFP.

For the FRET approaches, cells are washed twice with 2 ml PBS and then incubated for 1 h at 37° C. with 250 μl peptide solution. They are again washed twice with 2 ml PBS and then twice with 1 ml PBS, and then scraped in 1 ml PBS and centrifuged for 5 min at 1250 rpm. The supernatant is then aspirated and the cell pellet is lysed in 80 μl PBS+0.1% Triton X100. Twenty μl of each cell lysate is analyzed by measuring fluorescence emission after the FRET reaction.

Thus, experiments involving the incubation of peptides on various cells expressing hLDLR are performed demonstrating that the peptides bind to CHO-LDLR-GFP cells and that they undergo endocytosis to accumulate in the cells of the cell line that expresses hLDLR, which is not the case for the control peptides. In these experiments, preliminary incubation of peptides conjugated with STag, with a primary antibody (primary Ab) directed against STag, and a secondary antibody (secondary Ab) directed against the primary antibody, show that the complex between a peptide/STag, a primary Ab and a secondary Ab binds to cells expressing hLDLR and is internalized by endocytosis. These results indicate that the cyclic peptides of this family can bind to cells expressing hLDL and vectorize large loads (two antibodies), i.e., these loads are internalized by endocytosis.

Figure 8:
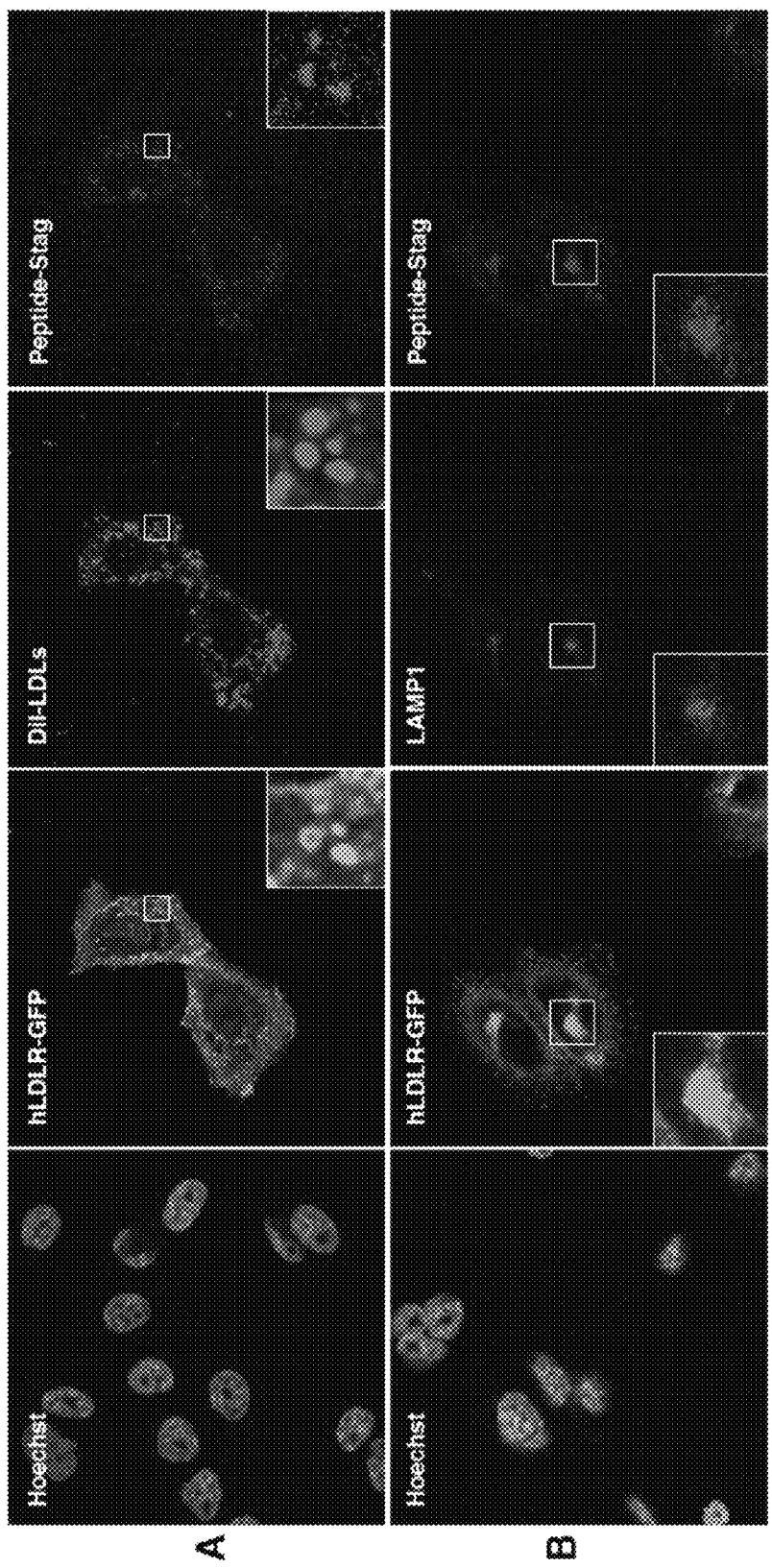
FIG. 8. A—Pulse-chase experiment using CHO-hLDLR-GFP cells grown on coverslips and incubated with DiI-LDL together with the peptide-STag conjugate (SEQ ID NO: 17). After 5 minutes incubation, cells are extensively washed and then incubated in chase media for 15 minutes. Nuclei are stained using Hoechst. Insets show higher magnification of a representative area of confocal images and indicate colocalization of the peptide with both the LDLR and LDL.

In order to further assess the precise subcellular trafficking of peptides conjugated to STag, pulse-chase experiments were performed in CHO-hLDLR-GFP cells (FIG. 8). In these experiments, the complex composed of peptide (SEQ ID NO: 17)-STag/primary antibody/secondary antibody is incubated with CHO-hLDLR-GFP cells for 5 minutes at 37° C. alone or together with LDLs, the natural ligand of LDLR, coupled to the fluorescent probe DiI (DiI-LDL). Cells are then washed 3 times with 1 ml PBS and incubated in chase media for 15 minutes, allowing accumulation of cytoplasmic endocytic vesicles, or for 1 hour, allowing trafficking and fusion of endosomes with lysosomes. Cells are then fixed with PFA 4% for 10 minutes and processed without permeabilization (FIG. 8-A) or permeabilized with PBS/Triton-X100 0.1% for 10 minutes before immunostaining of lysosomes (FIG. 8-B). The results indicate that i) this family of cyclic peptides are able to bind specifically hLDLR expressed at the surface of cells and undergo endocytosis without altering the binding and endocytosis of LDLs, the natural ligand of LDLR, ii) following endocytosis, these peptides use the same intracellular trafficking pathway than LDLs, ultimately leading to the fusion of peptide-containing vesicles with lysosomes.

Example V

Toxicity, endocytosis and transcytosis of synthesized peptides with affinity for hLDLR on endothelial cells in in vitro BBB models.

The potential toxic effects of peptides on endothelial cells, the binding/accumulation of peptides in these cells, and the passage by transcytosis of peptides are evaluated on in vitro BBB models. The cells necessary to set up the model (co-culture of endothelial cells from brain microvessels and astrocytes) are bovine cells (brain capillary endothelial cells, BCECs) sold by Cellial Technologies (Lens, France) or rat or mouse cells (rat or mouse BCECs) having made it possible to develop an internal murine model. This type of in vitro BBB model is used to evaluate the passive passage or active transport of numerous molecules, notably pharmacological agents, across BCECs and thus by extrapolation their capacity to reach CNS tissue in vivo. The bovine and murine models have ultrastructural properties characteristic of the brain endothelium, notably tight junctions, absence of fenestrations, absence of transendothelial channels, low permeability to hydrophilic molecules and high electrical resistance. Moreover, these models have shown solid correlations between the results of measurements taken on various molecules evaluated in vitro and in vivo for their property of passing across the BBB. To date, all the data obtained show that these in vitro BBB models closely imitate the situation in vivo by reproducing some of the complexities of the cell environment that exist in vivo, while preserving the advantages associated with cell culture experimentation.

For example, the in vitro bovine BBB model brings into play a co-culture of BCECs and astrocytes. Prior to cell culture, membrane inserts (Millicell-PC 3.0 μm; 30 mm diameter) are treated on the upper part with rat tail collagen in order to enable optimal adhesion of BCECs and to create the conditions of a basal lamina. Primary cultures of mixed astrocytes are established from neonatal rat cerebral cortex (Dehouck et al., 1990, *J. Neurochem.*, 54, 1798-1801). Briefly, after the meninges are removed, the brain tissue is passed through an 82 μm nylon sieve. The astrocytes are distributed in microplate wells at a concentration of $1.2 \times 10^5$ cells/ml with 2 ml optimal culture medium (DMEM) supplemented with 10% heat-inactivated fetal calf serum. The medium is changed twice per week. The BCECs obtained from Cellial Technologies are grown in the presence of DMEM medium supplemented with 10% (v/v) horse serum and 10% heat-inactivated calf serum, 2 mm glutamine, 50 μg/ml gentamicin and 1 ng/ml basic fibroblast growth factor, added every two days. The BCECs are then distributed on the upper surface of the filters in 2 ml co-culture. This BCECs medium is changed three times per week. Under these conditions, differentiated BCECs form a monolayer of confluent cells seven days later.

To test their toxicity, the inventive peptides coupled to rhodamine (TAMRA) are incubated in the upper chamber of the culture system, in contact with endothelial cells for 1 h, 5 h and 24 h. The culture medium of the lower chamber is collected at various times and fluorescence quantified by fluorimetric analysis. The results are expressed as endothelial surface permeability (Pe) in units of $10^{-3}$ cm/min. Lucifer Yellow (LY), a small fluorescent molecule which crosses the BBB very little, is used first to evaluate the integrity of the BBB in vitro, in all the wells analyzed, and second for peptide co-incubation in order to evaluate the absence of toxicity of the peptides for the endothelial cells that form this BBB. The culture media is collected at different time points and fluorescence is quantified by fluorimetry. Results are expressed as endothelial surface permeability (or Pe) in $10^{-3}$ cm/min. The in vitro barrier is considered "permeable" or "open" if the Pe value of LY is greater than $1 \times 10^{-3}$ cm/min. Transendothelial electrical resistance (TEER), measured with an ohmmeter and expressed in ohm·cm$^2$, also makes it possible to measure BBB integrity in vitro during tests of passage across the BBB. The quality threshold value is set at >500 ohm·cm$^2$.

The experiments carried out show an absence of toxicity of the peptides, as well as for the control peptide used, and an absence of deleterious effects on the permeability properties of the BBB.

The passage across the BBB of an inventive peptide conjugated to rhodamine (TAMRA) is verified on the in vitro bovine model described above. This analysis is carried out by measuring by fluorimetry the quantity of rhodamine accumulated in the receiver wells at various times (1 h, 4 h, 24 h). The integrity of the BBB in the various wells analyzed is evaluated by simultaneous measurement of the level of LY that passes from one compartment to the other as a function of time.

Example VI

Biomolecular and biochemical coupling of the peptide SEQ ID No: 31 and SEQ ID No: 17, respectively, to the human Fc fragment of an IgG1 antibody and evaluation of binding, endocytosis and RMT in a CHO hLDLR cell line and in vitro rat BBB model.

Some of the peptides having affinity for the hLDLR were tested for their ability to promote binding and/or endocytosis and/or transcytosis of the constant fragment of a human IgG1 antibody (Fc fragment) to hLDLR expressed in cell lines or in primary endothelial cells. For this purpose, the inventors either cloned the sequence encoding the peptide SEQ ID NO: 31 in fusion with the Fc fragment of a human IgG1, or chemically coupled peptide SEQ ID NO: 17 to the same antibody fragment.

In order to produce the constant fragment of human IgG1 fused to peptide SEQ ID: 31, a plasmid construct was generated based on the plasmid-pINFUSE hIgG1-Fc2 (InvivoGen) which was used as template. A mega-primer called Fc-SEQ ID NO: 31 was synthesized by PCR using the oligonucleotides:

```
Forward primer:
                                      (SEQ ID NO: 24)
CTTGGCATTATGCACCTCCA Reverse primer:
                                      (SEQ ID NO: 25)
CTGGCCAGCTAGCACTCAGCAACCGCGAAGACGAGGCATAC AAGCACCTTTACCCGGAGACAGGGAG
(primer containing the sequence coding for
the peptide SEQ ID NO: 31).
```

The product of the PCR reaction (Fc-SEQ ID NO: 31) was purified, digested with DpnI (enzyme that digests the parental methylated DNA) and used as a mega primer in a second PCR reaction performed with the pINFUSE hIgG1-Fc2 plasmid used as matrix using the QuickChange II Site Directed Mutagenesis Kit (Agilent). After transformation of competent bacteria, isolated colonies were obtained and plasmid DNA was prepared and the cDNA construct was sequenced on both strands for verification. This vector, called pFc-SEQ ID NO: 31, allows expression of an IgG1 Fc fragment fused in its N or C-terminus with the peptide SEQ ID NO: 31 after transfection of mammalian cells. Human embryonic Kidney cells (HEK 293) were transfected using lipofectamine 2000 (Invitrogen) with plasmid pFc-SEQ ID NO: 31. Seventy two hours post-transfection, protein Fc-SEQ ID NO: 31 contained in the culture supernatant was purified using the Prosep Protein A Purification Kit (Millipore). The purified fusion protein was assayed by a sandwich ELISA test and was subsequently used to carry out tests on hLDLR CHO cells, primary endothelial cells and in vitro BBB models.

For chemical coupling of the peptide SEQ ID NO: 17 to an IgG1 Fc fragment (Millipore), the Controlled Protein-Protein Crosslinking Kit (Thermo Scientific) was used. The peptide SEQ ID NO: 17 was synthesized to carry a free sulfhydryl group (cysteamide) available for linkage with a purified Fc fragment with maleimide groups added on primary amines of the Fc fragment. The number of moles of peptide per mole of Fc fragment was evaluated from 1 to 7. The obtained protein was named Fc-SEQ ID NO: 17 and was assayed by a sandwich ELISA test. It was subsequently used to perform tests on CHO hLDLR cells. The binding of Fc-SEQ ID NO: 31 and of Fc-SEQ ID NO: 17 was also assessed by immunocytochemistry (FIG. 8). At the concentration of 5 nM, both the fused peptide SEQ ID NO: 31 to the Fc fragment and the chemically bound peptide SEQ ID NO: 17 to the Fc fragment bind the hLDLR. No binding is observed for Fc alone. No binding is observed on CHO WT cells (not shown).

The rat BCEC from the in-vitro BBB model as described in Example V was used in binding/uptake and transport experiments of Fc-SEQ ID NO: 31 versus Fc fragment alone used as a negative control. The expression of the LDLR (FIG. 10) and its functionality for RMT (FIG. 12 C WT curve) in the in-vitro BBB model were assessed. Then, Fc-SEQ ID NO: 31 and Fc were incubated at 1 µM in co-incubation with DiI-LDL at 40 µg/mL during 30 min on live RBCEC at 37° C. Following this co-incubation, the cell monolayer was washed extensively and fixed with PFA at 4%. The cell monolayer was permeabilized with a solution of 0.1% Triton X100. Fc and Fc-SEQ ID NO: 31 were revealed using a primary antibody against the human Fc fragment. Then confocal microscopy was used to assess the co-localization between DiI-LDL vesicles and Fc-SEQ ID NO: 31 fluorescence (FIG. 11A to F). The same experiment was also performed with rat BCEC from LDLR −/− rats (KO) (SAGE laboratories from Sigma Aldrich). This experiment confirmed the role of the LDLR in DiI-LDL binding and endocytosis since DiI-LDL binding was not observed in rat BCEC lacking the LDLR. Concomitantly, staining for Fc-SEQ ID NO: 31 was not detected in BCEC form the LDLR KO rats.

In order to confirm the targeting of LDLR by the Fc-SEQ ID NO: 31 in the rat in-vitro BBB model, binding/uptake and transport experiments were performed with different concentrations of Fc and Fc-SEQ ID NO: 31 (FIG. 12). The graph in FIG. 12 A shows a significant difference of binding/uptake of the Fc-SEQ ID NO: 31 in comparison with the Fc fragment. Results are highly reinforced by the transport experiment (FIG. 12 B) showing a significant difference of accumulation of the Fc-SEQ ID NO: 31 versus the Fc fragment alone in the lower compartment of the in-vitro BBB model. As a control, DiI-LDL was also quantified in the lower compartment of the in-vitro BBB model (FIG. 12 C, WT curve). The graph shows a saturation of the transport at 4 µg per insert. In order to confirm the LDLR specificity of the signal that was quantified with the DiI-LDL and more specifically the Fc-SEQ ID NO: 31, these experiments were repeated with an in-vitro BBB model based on BCEC from the LDLR KO rats. The graphs from FIGS. 12 C and 12 D show that there is no DiI-LDL and Fc-SEQ ID NO: 31 transport across the BCEC monolayer into the lower compartment (significant differences between experiments with WT and LDLR KO BCEC).

Example VII

Protocols for chemical synthesis of conjugates comprised of a vector and a therapeutic molecule of interest or an imaging (or diagnostic) agent or any other molecule such as a molecular probe.

A therapeutic molecule of interest or an imaging or diagnostic agent or any other molecule such as a molecular probe can be cleaved/released/salted out from the vector after transport and passage across cell membranes, more particularly the BBB, for example through a prodrug strategy by hydrolysis or enzymatic cleavage of a chemical bond between the vector and the active substance.

Covalent coupling between the peptide vector completely protected on its reactive side functions (coupling at the C-term and N-term) or partially protected (coupling on a reactive function of a side chain) and the therapeutic molecule of interest is carried out via two general strategies (FIG. 2):
synthesis in tandem (i.e., direct coupling with no intermediate between the two entities),
synthesis via a linker (Temsamani et al., 2004, *Drug Discov. Today*, 23, 1012-1019).

According to the peptide vector and molecule of therapeutic interest selected, one or the other of the various strategies is applied either on the C-term, or on the N-term, or on a side chain reactive function of this peptide vector. Ideally, in a prodrug strategy, the spacers selected should enable suitable release of the active substance and improvement of the solubility of the conjugate (Molema et al., 2001, *Drug targeting, organ-specific strategies. In Methods and principles in medicinal chemistry*, vol. 12; Kratz et al., 2008, *Prodrug Strategies in Anticancer Chemotherapy. In ChemMedChem*, vol. 3). Various labile covalent chemical bonds can thus be generated between the two entities (vector and active substance) via or not via a spacer: amides, carbamates, esters, thioester, disulfide, etc. For example, it has been shown in the literature that disulfide bonds, relatively stable in plasma, can be cleaved, by enzymes such as protein-disulfide reductase, inside the intracerebral compartment to restore a free thiol function (Saito et al., 2003, *Adv. Drug Deliv. Rev.*, 55, 199-215).

Others compounds of interest are those wherein the spacer is a polymer such as polyethylene glycol (PEG). Indeed, it has been shown in the literature that the conjugation of an organic molecule of biological interest with PEG made it possible to increase the plasma half-life of this molecule (Greenwald et al., 2003, *Adv. Drug Deliv. Rev.*, 55, 217-250) and to decrease its clearance.

Another strategy consists in the use of acido-unstable linkers as for example the groupings cis-aconityl or hydrazone, stable in the plasma environment at pH 7.4 but cleaved in the acid environment of endosomes, where the pH is situated between 5.5 and 6.5 (D'Souza and Topp, 2001, *Release from Polymeric Prodrugs: Linkages and Their Degradation, In Journal of Pharmaceutical Science*, vol. 93). A third family of linkers of peptidic nature that resist plasma enzymes, but highly sensitive to lysosomal proteases such as cathepsin-B, can be used, for example the tetra-peptides GFAL et GFLG (Bildstein and al., 2011, *Prodrug-based Intracellular Delivery of Anticancer Agents, In Advanced Drug Delivery Review*, vol. 63).

Vectors conjugated with an active substance or a substance of interest can be used in the diagnosis, imaging or therapy of a pathology, lesion or disorder of the CNS for preparing a drug capable of crossing the BBB, a brain tumor or another type of cancer cell for preparing a drug capable of crossing cancer cell membranes, and/or infectious pathologies for preparing a drug capable of crossing cell membranes and to target the infected cells of bacterial, viral, parasitic or fungal infectious pathologies of the brain or other tissues.

Examples of active substances of therapeutic interest conjugated to peptide vectors of the invention include, but are not limited to doxorubicin and other cytotoxic agents, cytarabin-C (Ara-C), ribavirin, acyclovir, adefovir and other antiviral agents, prolyl-4-hydroxylase (P4H) inhibitors, Matrix Metalloproteinases (MMPs) and other anti-fibrotic agents, etc.

Example VIII

Tissue distribution of peptides or peptides conjugated to drugs of therapeutic interest, imaging (or diagnostic) agents or any other substance used as a tracer.

The distribution of peptides and peptide conjugates targeting the LDLR is assessed in mice to illustrate their ability to accumulate preferentially in tissues and organs expressing high levels of the target receptor.

Similar to brain perfusion experiments, peptides and peptide conjugates injected in mice are radiolabelled using tritium. Ten minutes after intravenous injection in the tail vein of wild-type mice or mice lacking the gene encoding LDLR (LDLR-KO mice), mice are sacrificed and the radioactivity present in the plasma and tissues is quantified. The results obtained using the peptide SEQ ID NO: 5 as an example illustrate the ability of this family of peptide vectors to target the LDLR in vivo and to accumulate preferentially in organs and tissues that are known to express high levels of the receptor and showing high LDL uptake (i.e. high receptor activity), including the liver, adrenal glands and the intestine, with a ≈5-fold, ≈2-fold and ≈6-fold decrease in peptide concentration, respectively, in LDLR-KO mice compared to wild-type mice.

Example IX

Brain perfusion in situ for vectors alone and vectors conjugated with a therapeutic molecule of interest or an imaging (or diagnosis) agent or any other molecule such as a molecular probe, and study of their transport kinetics across the BBB and their accumulation in the brain of mouse.

The in situ brain perfusion technique (in adult male OF1 mouse) is used to illustrate passage in the brain across the BBB.

Beforehand, the peptide vectors are radiolabelled with tritium ($^3$H), an element that offers the strongest sensitivity for the detection of radioactive compounds, notably on tissue sections. Radioactive peptides with high specific radioactivity (RAS, up to 100 Ci/mmol) are prepared by a strategy of acylation of the N-term amine function by tritiated propionic (or propanoic) anhydride or tritiated N-propionyl-succinimide (NPS). This tritiation method can be applied to all peptides (vectors, or conjugates between a therapeutic peptide and a peptide vector in tandem or via a linker (of peptide or organic nature)), provided that modification of the N-term does not affect the affinity of the peptides for the targeted receptor (i.e., LDLR) or their biological activity in the case of therapeutic peptides.

The tritiation reaction of the peptide vector in the N-term position by propionylation is carried out in DMF (1 mg peptide in 100 µl to 450 µl according to solubility) by adding 0.1 equivalent of tritiated NPS for 5 min at room temperature, then 0.9 equivalent of cold NPS (non-tritiated) for 1 h, and then a new equivalent of cold NPS for 5 h. The reaction medium is then left at 4° C. overnight and purified the following day by HPLC. The RAS for each tritiated peptide is typically between 5 Ci/mmol and 60 Ci/mmol. The total quantity of radioactivity prepared by synthesis is generally between 500 µCi and 1000 µCi.

Radiolabelled peptides (radiolabelled with $^3$H, for example) are coupled covalently with a radiolabelled active substance (radiolabelled with $^{14}$C, for example) as described for example in EXAMPLE VII. As previously mentioned, this covalent coupling is carried out according to the structure and physicochemical properties of the active substance, in particular the presence of functional chemical groups that can be modified without decreasing the biological activity of this substance. Radiolabelled conjugates are synthesized by extrapolation from synthetic pathways developed for non-radiolabelled conjugates.

The techniques briefly summarized below were developed previously to study the distribution in the brain of active substances and, in particular, the role of the BBB and, more particularly, of LDLR in the penetration of these molecules in the brain. In situ brain perfusion techniques are among the most technically demanding and the most difficult to perform in the mouse. However, in situ brain perfusion (like in vitro models) enables total control of the composition of the artificial perfusate in order to maintain the cells and vascularization of the brain under normal physiological and anatomical conditions within the animal, without the disrupting factor of systemic distribution.

This strategy of in situ brain perfusion normally carried out in the rat was adapted for mouse (Dagenais et al., 2000, *J Cereb Blood Flow Metab.*, 20(2), 381-6) in order to broaden its application for evaluating the parameters of transport kinetics at the BBB and the blood-retinal barrier, and this also in transgenic and KO mutant mice for the receptors, enzymes or transporters of active substances. It involves catheterization of a carotid artery in anaesthetized mice (typically OF1) and ligature of certain branches of this carotid artery (external, thyroidal, occipital) in order to specifically perfuse the internal carotid and pterygopalatine arteries, which are used to evaluate the uptake in the brain of the vectors and conjugates. The catheter makes it possible to replace general circulation by infusion with a well-controlled perfusate (bicarbonate buffer, plasma or blood) by passing by the carotid. Oxygenated Krebs bicarbonate buffer is first used to evaluate the capacities of the vectors and conjugates to pass in the brain. After catheterization of the carotid, endogenous blood flow is stopped by sectioning the ventricles of the heart in order to avoid the mixture of buffer with blood and elevation in blood pressure. The duration of the fixed flow-rate perfusion is monitored. The buffer perfusion can be extended up to 20 min, or up to 1 h in the presence of oxygen transporters (washed erythrocytes) for studies of receptor-mediated transport (RMT).

The experiments carried out made it possible to establish cerebral transport, or the transfer coefficient ($K_{in}$: relationship between distribution volume and cerebral perfusion time), of several peptide vectors and conjugates of the invention. The duration of brain perfusion for these experiments is 2-5 min with a perfusate flow rate of 2 ml/min.

For example, the Kin of the opiate peptide Dalargine, conjugated to SEQ ID NO:17 was $\approx 20 \times 10^{-4}$ ml/s/g while the Kin of Dalargine alone was $\approx 0.9 \times 10^{-4}$ ml/s/g.

For comparison, Tf, the natural ligand of the TfR has a Kin of $3.0 \times 10^{-4}$ ml/s/g (Demeule et al., 2008, *J. Neurochem.*, 106 (4), 1534-1544).

These results thus show that the conjugates of the invention, due to their small size and advantageous configuration, have a cerebral transfer coefficient greater than that of Tf.

We claim:

1. A linear or cyclic peptide or pseudo-peptide comprising formula (I):

A1-Met-A2-Arg-Leu-Arg-A3-A4     (I)

wherein A1 is cysteine, (D)-cysteine ((D)-Cys), penicillamine (Pen) or (D)-penicillamine ((D)-Pen); A2 is proline, pipecolic acid (Pip) or thiazolidine-4-carboxylic acid (Thz); A3 is glycine or sarcosine (Sar); and A4 is cysteine, (D)-cysteine ((D)-Cys), penicillamine (Pen) or (D)-penicillamine (D-Pen).

2. The linear or cyclic peptide or pseudo-peptide of claim 1, wherein A1 is (D)-Cys, penicillamine (Pen) or (D)-penicillamine (D-Pen).

3. The linear or cyclic peptide or pseudo-peptide of claim 1, wherein A2 is pipecolic acid (Pip) or thiazolidine-4-carboxylic acid (Thz).

4. The linear or cyclic peptide or pseudo-peptide of claim 1, wherein A3 is sarcosine (Sar).

5. The linear or cyclic peptide or pseudo-peptide of claim 1, wherein the peptide or pseudo-peptide has a sequence selected from SEQ ID NOs: 1 to 9 and SEQ ID NOs: 26 to 30.

6. The linear or cyclic peptide or pseudo-peptide of claim 1, wherein the peptide has a cyclic configuration.

7. The linear or cyclic peptide or pseudo-peptide of claim 1, wherein said peptide or pseudo-peptide contains at least one peptidomimetic bond, chosen from intercalation of a methylene ($—CH_2—$) or phosphate ($—PO_2—$) group, secondary amine ($—NH—$) or oxygen ($—O—$), alpha-azapeptides, alpha-alkylpeptides, N-alkylpeptides, phosphonamidates, depsipeptides, hydroxymethylenes, hydroxyethylenes, dihydroxyethylenes, hydroxyethylamines, retro-inverso peptides, methyleneoxy, cetomethylene, esters, phosphinates, phosphinics, phosphonamides or a carba group.

8. The linear or cyclic peptide or pseudo-peptide of claim 1, wherein the peptide or pseudo-peptide has an N-terminus protected by acylation and/or C-terminus (C-term) protected by amidation or esterification.

9. A conjugated compound of following formula (III):

VxLzDy     (III)

wherein V is a linear or cyclic peptide or pseudo-peptide according to claim 1, L is a linker or a spacer, D is a substance of interest, x and y are integers between 1 and 5 and z is 0 or 1, wherein, D is coupled with V, optionally via L, at one or more reactive groups at one or more N-term and/or C-term ends of V and/or at one or more reactive groups carried by the natural or non-natural amino acid side chains of V and wherein the substance of interest is a therapeutic agent, a diagnostic agent, a medical imaging agent, a molecular probe, a small molecule chemical, a peptide, a protein, an antigen, an antibody, a part of an antibody, a nucleic acid, an oligonucleotide or a ribozyme.

10. The conjugated compound of claim 9, wherein x=z=y=1; or z is 0 and x and y are 1; or y is greater than x.

11. The conjugated compound of claim 9, wherein the coupling between V and D, or between V and L on the one hand and L and D on the other, is carried out by one or more covalent, ionic, hydrogen, hydrophobic or Van der Waals bonds.

12. A method for preparing a conjugated compound compound comprising a coupling step between a peptide or pseudo-peptide of claim 1 and a substance D, optionally via a linker L, by chemical, biochemical or enzymatic route or by genetic engineering.

13. A pharmaceutical composition comprising at least one conjugated compound of claim 9 and one or several pharmaceutically acceptable excipients.

14. A diagnostic composition comprising the conjugated compound of claim 9.

15. A method for delivering a molecule to a subject comprising administering to the subject said molecule coupled to a peptide or pseudo-peptide of claim 1.

16. The peptide or pseudo-peptide of claim 1, wherein A4 is cysteine (Cys) or penicillamine (Pen).

17. The peptide or pseudo-peptide of claim 1, wherein A1 is D-penicillamine (D-Pen) or D-cysteine (D-cys); A2 is pipecolic acid (Pip) or thiazolidine-4-carboxylic acid (Thz); A3 is glycine or sarcosine (Sar); and A4 is cysteine (Cys) or penicillamine (Pen).

18. The peptide or pseudo-peptide of claim 1, wherein said peptide or pseudo-peptide is directly or indirectly conjugated to an active substance and wherein the active substance is a therapeutic agent, a diagnostic agent, a medical imaging agent, a molecular probe, a small molecule chemical, a peptide, a protein, an antigen, an antibody, a part of an antibody, a nucleic acid, an oligonucleotide or a ribozyme.

* * * * *

UNITED STATES PATENT AND TRADEMARK OFFICE
CERTIFICATE OF CORRECTION

PATENT NO. : 8,877,716 B2
APPLICATION NO. : 13/655954
DATED : November 4, 2014
INVENTOR(S) : Patrick Vlieghe et al.

It is certified that error appears in the above-identified patent and that said Letters Patent is hereby corrected as shown below:

In the Specification

Column 8,
Line 21, "formula (I'):" should read --formula (I"):--.
Line 23, "A1-Met-A2-Arg-Leu-Arg-Ala-A4     (I')" should read
    --A1-Met-A2-Arg-Leu-Arg-Ala-A4     (I")--.

Column 21,
Line 5, "Cho Cell Lines" should read --CHO Cell Lines--.

Column 23,
Lines 63-64, "art: $H_2O/AcOH/ANH_4)_2CO_3/DMSO$, $H_2O/AcOHANH_4)_2CO_3$," should read
    --art: $H_2O/AcOH/,/(NH_4)_2CO_3/DMSO$, $H_2O/AcOH,/(NH_4)_2CO_3$,--.

In the Claims

Column 50,
Lines 28-29, Claim 12, "conjugated compound compound comprising" should read
    --conjugated compound comprising--.

Signed and Sealed this
Twenty-third Day of June, 2015

Michelle K. Lee
*Director of the United States Patent and Trademark Office*